United States Patent
Qiu et al.

(10) Patent No.: US 12,082,610 B2
(45) Date of Patent: Sep. 10, 2024

(54) CARTRIDGE AND ELECTRONIC CIGARETTE

(71) Applicant: CHANGZHOU PATENT ELECTRONIC TECHNOLOGY CO., LTD, Changzhou (CN)

(72) Inventors: Weihua Qiu, Jiangsu (CN); Xing Liu, Jiangsu (CN); Guangxian Huang, Jiangsu (CN)

(73) Assignee: CHANGZHOU PATENT ELECTRONIC TECHNOLOGY CO., LTD, Changzhou (CN)

( * ) Notice: Subject to any disclaimer, the term of this patent is extended or adjusted under 35 U.S.C. 154(b) by 735 days.

(21) Appl. No.: 17/240,972

(22) Filed: Apr. 26, 2021

(65) Prior Publication Data

US 2021/0298356 A1  Sep. 30, 2021

Related U.S. Application Data

(63) Continuation-in-part of application No. PCT/CN2019/110692, filed on Oct. 12, 2019.

(30) Foreign Application Priority Data

Oct. 26, 2018  (CN) .......................... 201811261667.1
Oct. 26, 2018  (CN) .......................... 201821749450.0

(51) Int. Cl.
*A24F 40/42* (2020.01)
*A24F 7/00* (2006.01)
(Continued)

(52) U.S. Cl.
CPC ................ *A24F 40/42* (2020.01); *A24F 7/00* (2013.01); *A24F 40/10* (2020.01); *A24F 40/44* (2020.01);
(Continued)

(58) Field of Classification Search
CPC .......... A24F 40/10; A24F 40/44; A24F 40/46; A24F 40/485; A24F 40/51; A24F 40/40; A24F 40/42; A24F 7/00; B65B 39/00
See application file for complete search history.

(56) References Cited

U.S. PATENT DOCUMENTS 10,051,894 B2 *  8/2018  Gavrielov ............... A24F 40/46
10,196,188 B2 *  2/2019  Liu .......................... A24F 40/42
(Continued)

FOREIGN PATENT DOCUMENTS

CN        204393354 U      6/2015
CN        204146318 U     12/2015
(Continued)

OTHER PUBLICATIONS

The extended European search report of EP application No. 19877517.3 issued on Oct. 17, 2022.

*Primary Examiner* — Marcus E Harcum
(74) *Attorney, Agent, or Firm* — Andrew C. Cheng

(57) ABSTRACT

A cartridge includes a cartridge casing with a liquid storage chamber therein, a sealing member for sealing the liquid storage chamber, a shielding member provided on the cartridge casing, an atomizing chamber, a smoke outlet channel and an air inlet passage. The sealing member is located between the shielding member and the cartridge casing. The shielding member forms part of the outer contour of the cartridge and the sealing member is shielded by the shielding member. A communication opening is defined through the shielding member. The sealing member is an elastically deformable member. When filling liquid, a liquid injection needle passes through the communication opening and pierces the sealing member, and then extends into the liquid storage chamber to inject e-liquid. When the liquid injection needle is pulled out after liquid injection, the sealing mem- (Continued)

ber automatically restores to seal the liquid storage chamber again.

11 Claims, 17 Drawing Sheets

(51) Int. Cl.
*A24F 40/10* (2020.01)
*A24F 40/44* (2020.01)
*A24F 40/46* (2020.01)
*A24F 40/485* (2020.01)
*A24F 40/51* (2020.01)
*B65B 39/00* (2006.01)

(52) U.S. Cl.
CPC ............ *A24F 40/46* (2020.01); *A24F 40/485* (2020.01); *A24F 40/51* (2020.01); *B65B 39/00* (2013.01)

(56) References Cited

U.S. PATENT DOCUMENTS

| | | | | |
|---|---|---|---|---|
| 10,865,001 | B2* | 12/2020 | Atkins | B65B 3/18 |
| 11,147,314 | B2* | 10/2021 | Qiu | A61M 11/042 |
| 2015/0059787 | A1* | 3/2015 | Qiu | A24F 40/46 |
| | | | | 392/395 |
| 2016/0286860 | A1 | 10/2016 | Flayler | |
| 2017/0238617 | A1* | 8/2017 | Scatterday | A24F 40/42 |
| 2017/0276342 | A1 | 9/2017 | Chen et al. | |
| 2018/0263294 | A1* | 9/2018 | Qiu | A24F 47/00 |
| 2019/0021398 | A1* | 1/2019 | Qiu | A24F 40/485 |
| 2019/0046745 | A1* | 2/2019 | Nettenstrom | A61M 11/042 |
| 2019/0373679 | A1* | 12/2019 | Fu | A24F 7/00 |
| 2020/0022417 | A1* | 1/2020 | Atkins | A61M 15/0063 |
| 2020/0022418 | A1* | 1/2020 | Belisle | A24F 47/00 |
| 2020/0113246 | A1* | 4/2020 | Barbaric | A24F 40/53 |
| 2023/0319953 | A1* | 10/2023 | Bowen | A24F 40/42 |
| | | | | 131/329 |

FOREIGN PATENT DOCUMENTS

| | | |
|---|---|---|
| CN | 205695715 U | 11/2016 |
| CN | 206620829 U | 11/2017 |
| CN | 109700075 A | 5/2019 |
| CN | 209219272 U | 8/2019 |
| CN | 209314958 U | 8/2019 |
| CN | 209420953 U | 9/2019 |
| CN | 209420954 U | 9/2019 |
| WO | 2013110210 A1 | 8/2013 |
| WO | 2017139595 A1 | 8/2017 |
| WO | WO-2018095243 A1 * | 5/2018 ............. A24F 47/00 |

* cited by examiner

CARTRIDGE AND ELECTRONIC CIGARETTE

CROSS-REFERENCE TO RELATED APPLICATIONS

This application is a continuation-in-part of International patent application No. PCT/CN2019/110692, filed on Oct. 12, 2019, entitled "cartridge and electronic cigarette", which claims priority to Chinese patent application Nos. 201811261667.1 and 201821749450.0, filed on Oct. 26, 2018. All of the aforementioned patent applications are hereby incorporated by reference in their entireties.

TECHNICAL FIELD

The present disclosure relates to the technical field of simulated smoking, and more particularly, relates to a cartridge and an electronic cigarette having the cartridge.

BACKGROUND

The electronic cigarette includes a cigarette cartridge and a battery assembly electrically connected with the cigarette cartridge. There is an atomizer located in the cartridge, the atomizer heats the e-liquid stored in the cartridge under the electric driving of the battery assembly, so that the e-liquid is heated to generate smoke, and the smoke can be inhaled by the user.

For the liquid injection operation of existing cartridges, firstly, most of them need to remove the sealing element to expose the liquid injection hole, then inject e-liquid into the liquid storage chamber through the liquid injection hole. After the liquid injection is completed, the sealing element must be installed in the liquid injection hole again to prevent the e-liquid from leaking. Therefore, whether for users or manufacturers, the injection process is relatively cumbersome. In addition, since the sealing element is generally soft, it is difficult to be clamped by an equipment and automatically installed by the equipment. Therefore, it is difficult for manufacturers to realize automatic operation with this injection method.

SUMMARY

In order to solve the problem that the green indicator light of the electronic device in the prior art is difficult to accurately indicate whether the battery assembly is fully charged, the embodiment of the present disclosure provides a charging state indicating circuit and an electronic device. The technical solution is as follows:

In the first aspect, a charging state indicating circuit is provided, which includes: a first color LED D5, a second color LED D4, a diode D3, a first resistor R15, and a second resistor R5, wherein:
  the anode of the first color LED D5 is electrically connected to a power supply through the first resistor R15, the cathode of the first color LED D5 is electrically connected to the charging state indicating terminal 11 of the charging chip U3; one end of the second resistor R5 is electrically connected to the power supply, and the other end of the second resistor R5 is electrically connected to the anode of the diode D3, the cathode of the diode D3 is electrically connected to the charging state indicating terminal 11; the other end of the second resistor R5 is also electrically connected to the anode of the second color LED D4, and the cathode of the second color LED D4 is grounded;
  the charging chip U3 outputs a low voltage through the charging state indicating terminal 11 during the charging process to light up the first color LED D5; the charging chip U3 controls the charging state indicating terminal 11 to be in a high impedance state when the battery assembly is fully charged, so as to light up the second color LED D4.

Optionally, the first color LED D5 and the second color LED D4 are packaged in a lamp group.

Optionally, the charging state indicating circuit further includes an overvoltage protection chip U7 and a connector J2, the first power receiving terminal 14 of the overvoltage protection chip U7 is connected to the power output terminal 15 of the connector J2, the state indicating terminal 16 of the overvoltage protection chip U7 is electrically connected to the enabling terminal 13 of the charging chip U3, the voltage detection terminal 18 of the overvoltage protection chip U7 is grounded through a third resistor;
  when the voltage on the voltage detection terminal 18 of the overvoltage protection chip U7 reaches the reference voltage, the state indicating terminal 16 outputs a high level to stop the charging chip U3 from working, the state indicating terminal 16 is active at a low level;
  when the voltage on the voltage detection terminal 18 of the overvoltage protection chip U7 is lower than the reference voltage, it outputs a low level through the state indicating terminal 16 to make the charging chip U3 work.

Optionally, the state indicating terminal 16 of the overvoltage protection chip U7 is grounded through a third color LED.

Optionally, the charging state indication circuit further includes a battery protection chip U1, the battery protection chip U1 includes a second power receiving terminal 41, a ground terminal 42, and a charging detection terminal 43;
  the second power receiving terminal 41 of the battery protection chip U1 is connected to the positive electrode of the battery assembly, the second ground terminal of the battery protection chip U1 is connected to the negative electrode of the battery assembly, the ground terminal 42 of the battery protection chip U1 is connected to the negative electrode of the battery assembly.

Optionally, the charging chip U3 includes a third power receiving terminal 12, a charging voltage output terminal 10, the third power receiving terminal 12 of the charging chip U3 is electrically connected to the external power supply through the connector J2, the charging voltage output terminal 10 is used to output the charging voltage to the positive electrode of the battery assembly.

Optionally, the charging state indicating circuit further includes a control chip U6 and a buck switch chip U2, the control chip U6 includes a first control signal input terminal 20 and a modulation signal output terminal 23, the first control signal input terminal 20 is electrically connected to the first control signal output terminal 24 of the suction detection element J3;
  the buck switch chip U2 includes a first conducting terminal 26, a first control terminal 27, and a second conducting terminal 28, the first conducting terminal 26 of the buck switch chip U2 receives the system power supply voltage, the first control terminal 27 of the buck switch chip U2 is connected to the modulation signal output terminal 23 of the control chip U6;

when the first control signal input terminal 20 receives an effective level, the modulation signal output terminal 23 of the control chip U6 outputs a pulse modulation signal to the first control terminal 27 of the buck switch chip U2; when the first control terminal 27 of the buck switch chip U2 receives a pulse width modulation signal of an effective level, control the conduction between the first conducting terminal 26 and the second conducting terminal 28, so that the second conducting terminal 28 outputs the driving voltage whose voltage value is less than the voltage value of the system power supply voltage.

Optionally, the control chip U6 further includes a second control signal input terminal, the second control signal input terminal of the control chip U6 is connected to the second control signal output terminal 37 of the touch sensor chip U8, the touch input pin 25 of the touch sensor chip U8 is connected to a touch pad;

when the second control signal input terminal receives the effective level, the modulation signal output terminal 23 of the control chip U6 outputs the pulse modulation signal to the first control terminal 27 of the buck switch chip U2.

Optionally, the first enable signal output terminal of the control chip U6 is electrically connected to the second control terminal 30 of the first switching element Q11, the third conducting terminal 29 of the first switching element Q11 is grounded, the fourth conducting terminal 18 of the first switching element Q11 is electrically connected to the negative terminal of the motor, the positive terminal of the motor receives the system power supply voltage;

when the second control signal input terminal receives the effective level, the first switching element Q11 controls the third conducting terminal 29 and the fourth conducting terminal 18 to be conducted according to the enable signal provided by the first enable signal output terminal of the control chip U6, so that the motor is energized to work.

In a second aspect, an electronic device is provided, and the electronic device includes the charging state indication circuit involved in any one of the implementations of the first aspect.

The beneficial effects brought about by the technical solutions provided by the embodiments of the present disclosure are:

by providing a charging state indicator circuit, which includes a first color LED D5, a second color LED D4, a diode D3, a first resistor R15, and a second resistor R5, wherein: the anode of the first color LED D5 is electrically connected to a power supply through the first resistor R15, the cathode of the first color LED D5 is electrically connected to the charging state indicating terminal 11 of the charging chip U3; one end of the second resistor R5 is electrically connected to the power supply, and the other end of the second resistor R5 is electrically connected to the anode of the diode D3, the cathode of the diode D3 is electrically connected to the charging state indicating terminal 11; the other end of the second resistor R5 is also electrically connected to the anode of the second color LED D4, and the cathode of the second color LED D4 is grounded; the charging chip U3 outputs a low voltage through the charging state indicating terminal 11 during the charging process to light up the first color LED D5; the charging chip U3 controls the charging state indicating terminal 11 to be in a high impedance state when the battery assembly is fully charged, so as to light up the second color LED D4. The problem that the green indicator light of the current electronic device is difficult to accurately indicate whether the battery assembly is fully charged is solved; the effect of accurately prompting the charging state of the battery assembly is achieved.

In view of at least one of the above technical problems, it is necessary to provide a cartridge that is convenient for liquid injection.

It is also necessary to provide an electronic cigarette with the cartridge.

The technical solutions adopted by the present disclosure to solve its technical problems are:

A cartridge includes a cartridge casing with a liquid storage chamber therein, a sealing member for sealing the liquid storage chamber, a shielding member provided on the cartridge casing, an atomizing chamber, a smoke outlet passage, and an air inlet passage. The atomizing chamber is in communication with the liquid storage chamber, the smoke outlet passage and the air inlet passage. The sealing member is located between the shielding member and the cartridge casing. The shielding member forms part of the outer contour of the cartridge and the sealing member is shielded by the shielding member. A communication opening is defined through the shielding member. The sealing member is an elastically deformable member. When filling liquid, a liquid injection needle passes through the communication opening and pierces the sealing member, and then extends into the liquid storage chamber to inject e-liquid, and the air in the liquid storage chamber enters into the atomizing chamber and is discharged through the air inlet passage and/or the smoke outlet passage. When the liquid injection needle is pulled out after liquid injection, the sealing member automatically restores to seal the liquid storage chamber again.

Further, the cartridge further includes a mouthpiece and a bottom base. The mouthpiece is arranged at one end of the cartridge casing along the axial direction of the cartridge casing. The mouthpiece is provided with a smoke outlet opening. The bottom base is arranged at the other end of the cartridge casing along the axial direction of the cartridge casing opposite to the mouthpiece. The liquid storage chamber is provided in the cartridge casing along the axial direction of the cartridge casing. One of the mouthpiece and the bottom base serves as the shielding member.

Further, the cartridge further comprises a liquid guiding member, the liquid guiding member is made of porous material, the liquid guiding member is a hollow structure with both ends being opened, an inner cavity of the liquid guiding member forms the atomizing chamber, the liquid guiding member is arranged along the axial direction of the cartridge casing, the liquid guiding member is at least partially received in the liquid storage chamber, the liquid guiding member is located at one end of the liquid storage chamber adjacent to the bottom base, the smoke outlet passage is located in the liquid storage chamber and is isolated from the liquid storage chamber.

Further, the cartridge further includes a sealing element arranged between the mouthpiece and the cartridge casing. The mouthpiece is used as the shielding member, the sealing element is used as the sealing member, and the smoke outlet opening is used as the communication opening.

Further, the cartridge casing is provided with two liquid injection holes arranged symmetrically about the center axis of the cartridge. The liquid injection holes are in communication with the liquid storage chamber. The lower end surface of the sealing element is protruded to provide with two sealing portions for respectively sealing the two liquid injection holes. The upper end surface of the sealing element is provided with two liquid injection grooves corresponding to the two sealing portions. There are two smoke outlet openings on the mouthpiece, and the two smoke outlet openings are respectively aligned with the two liquid injection grooves.

Further, the cartridge further includes a sealing plug and a vent pipe. The sealing plug seals one end of the liquid storage chamber adjacent to the bottom base. The sealing plug is located between the cartridge casing and the bottom base. The vent pipe is received in the liquid storage chamber, one end of the vent pipe is connected with the liquid guiding member, and the other end of the vent pipe is connected with one end of the cartridge casing provided with the mouthpiece. The smoke outlet passage is formed by the inner cavity of the vent pipe.

Further, one end of the vent pipe is sleeved outside the liquid guiding member, the vent pipe is provided with a liquid intake hole in communication with the liquid storage chamber, the liquid guiding member is attached to the inner wall of the vent pipe corresponding to the liquid intake hole, or, one end of the vent pipe resists against the liquid guiding member, the outer peripheral wall of the liquid guiding member is exposed in the liquid storage chamber.

Further, an air inlet chamber separated from the liquid storage chamber is provided in the cartridge casing along the axial direction of the cartridge casing. The side wall of the cartridge casing is provided with an air inlet hole. A ventilation gap is formed between the bottom base and the sealing plug. The air inlet chamber is in communication with the air inlet hole and the ventilation gap respectively. The air inlet passage includes the air inlet hole, the air inlet chamber and the ventilation gap.

Further, the bottom base is used as the shielding member, the sealing plug is used as the sealing member, and the communication opening is defined through the bottom base.

Further, the cartridge further includes a magnetic attraction member arranged on the bottom base.

Further, a sensing passage separated from the liquid storage chamber and the air inlet chamber is provided in the cartridge casing along the axial direction of the cartridge casing. A sensing aperture is defined in the bottom base. The sensing passage is in communication with the sensing aperture and the smoke outlet opening.

An electronic cigarette includes any one of the above cartridges.

The beneficial effects of the present disclosure are: in the cartridge or electronic cigarette provided by the present disclosure, after the cartridge is assembled, a liquid injection needle is used to pierce the sealing element for performing liquid injection. After the liquid injection is completed, the liquid injection needle is pulled out, and the sealing element restores to seal by itself, which is convenient for users and manufacturers to perform liquid injection operations, and for manufacturers to realize automatic liquid injection. The above process can be realized without disassembling the cigarette, and the operation is simple and convenient to use.

A cartridge is provided for use in an electronic cigarette having a battery assembly. The cartridge includes an atomizing assembly, and the atomizing assembly includes an atomizer, a conductive sheet, a first electrode and a second electrode. The atomizer includes a heating member. Two ends of the heating member are respectively in contact with the first electrode and the second electrode to achieve electrical connection. The conductive sheet is in contact with the second electrode to achieve electrical connection. The conductive sheet is insulated from the first electrode to achieve electrical isolation. The battery assembly is provided with a first terminal and a second terminal. When the cartridge is connected to the battery assembly, the first terminal is electrically connected to the first electrode, and the second terminal is electrically connected to the conductive sheet.

Further, the cartridge includes a bottom base. The lower end surface of the bottom base is partially recessed to form a holding groove. The conductive sheet is installed in the holding groove. The first electrode and the second electrode are both inserted into the bottom base from the lower end surface of the bottom base and extend through the bottom base from the upper end surface of the bottom base. The second electrode is located at one side of the first electrode. The conductive sheet is sleeved on the outside of the second electrode. The conductive sheet extends to the other side of the first electrode after bypassing the first electrode.

Further, the bottom base has insulation properties, a part of the lower end surface of the bottom base is interposed between the conductive sheet and the first electrode.

Further, the upper end of each of the first electrode and the second electrode is provided with an opening, two ends of the heating member respectively extend into the opening of the first electrode and the opening of the second electrode, when a clamping force is applied to the opening of the first electrode and the opening of the second electrode, the opening of the first electrode and the opening of the second electrode clamp both ends of the heating member; or, the two ends of the heating member are respectively sandwiched between the first electrode and the bottom base, and the second electrode and the bottom base.

Further, the atomizing assembly includes a sealing plug and a vent pipe. The atomizing member further includes a liquid guiding member. The sealing plug is arranged on the bottom base. A ventilation gap exists between the sealing plug and the bottom base. One end of the vent pipe is arranged on the sealing plug. The liquid guiding member is accommodated in one end of the vent pipe adjacent to the sealing plug. The inner cavity of the liquid guiding member forms the atomizing chamber. The heating member is received in the atomizing chamber. The inner cavity of the vent pipe forms the smoke outlet passage. The atomizing chamber is in communication with the smoke outlet passage and the ventilation gap.

Further, the bottom base is provided with a sensing aperture isolated from the ventilation gap.

An electronic cigarette includes a battery assembly and any one of the above cartridges, the battery assembly is provided with the first terminal and the second terminal.

Further, the battery assembly includes a battery casing and a battery holder housed in the battery casing. The first terminal and the second terminal are both arranged on the upper end surface of the battery holder. When the cartridge is inserted into the battery casing, the lower end surface of the cartridge resists against the upper end surface of the battery holder.

Further, the upper end surface of the battery holder is provided with a first magnetic member corresponding to the second electrode. When the cartridge is inserted into the battery casing, the first magnetic member magnetically attracts the second electrode.

Further, the battery holder is provided with a second magnetic member, the second magnetic member is sleeved on the outer circumference of the second terminal. When the cartridge is inserted into the battery casing, the second magnetic member magnetically attracts the conductive sheet.

The beneficial effects of the present disclosure are: in the cartridge or electronic cigarette provided by the present disclosure, by setting the conductive sheet, it makes the installation of the first electrode, the second electrode, the first terminal and the second terminal more flexible, and can be customized according to the actual needs of the user.

BRIEF DESCRIPTION OF THE DRAWINGS

The present disclosure will be further described hereinafter with reference to the drawings and the embodiments.

FIG. 1-2 is a circuit diagram of the voltage output circuit in the charging state indication circuit provided by the present disclosure;

FIG. 1-3 is a circuit diagram of another charging state indicating circuit provided by the present disclosure;

FIG. 1-4 is a schematic diagram of the pins of the touch chip provided by the present disclosure;

FIG. 1-5 is a schematic diagram of a motor connection provided by an embodiment of the present disclosure;

FIG. 1-6 is a schematic diagram of the pins of a battery protection chip provided by an embodiment of the present disclosure;

FIG. 2-1 is a perspective view of an electronic cigarette of the second embodiment of the present disclosure;

FIG. 2-2 is another perspective view of the electronic cigarette of the second embodiment of the present disclosure;

FIG. 2-3 is a top view of the electronic cigarette of the second embodiment of the present disclosure;

FIG. 3 is an exploded view of the electronic cigarette shown in FIG. 2;

FIG. 4 is an exploded view of the cartridge of the electronic cigarette shown in FIG. 3;

FIG. 5 is a perspective view of the cartridge casing in the cartridge shown in FIG. 4;

FIG. 6 is a perspective view of the cartridge casing in the cartridge shown in FIG. 4 from another viewing angle;

Figure 1:
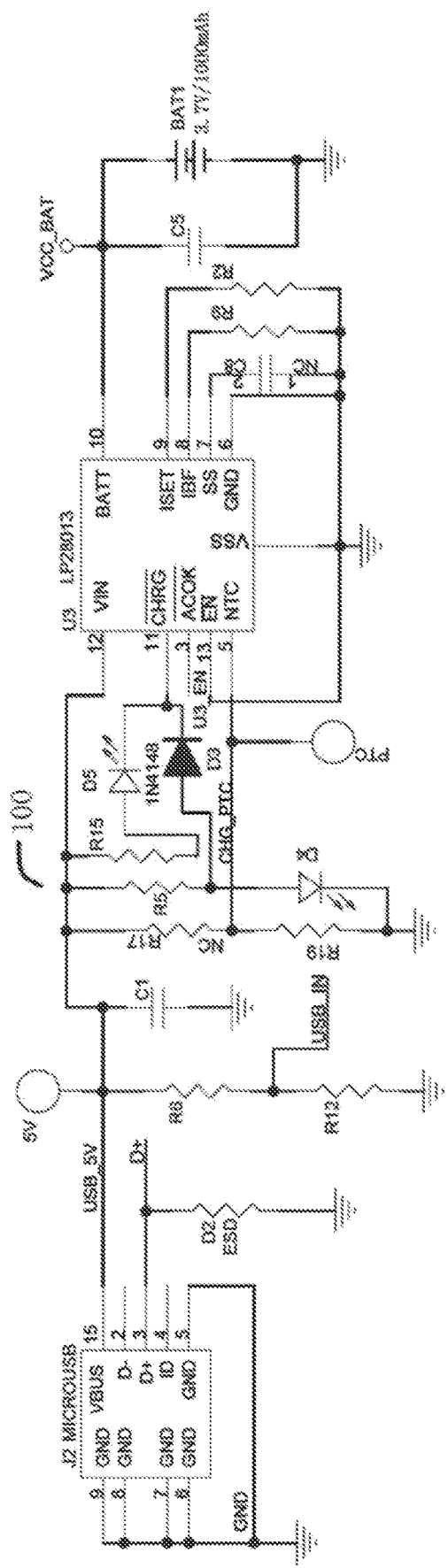
FIG. 1-1 is a circuit diagram of a charging state indicating circuit provided by the present disclosure.

The various components and reference numerals are as follow:

| | | |
|---|---|---|
| cartridge 50, 500 | cartridge casing 51 | first partition plate 511 |
| second partition plate 512 | liquid storage chamber 510 | sensing chamber 514 |
| air inlet chamber 513 | receiving groove 515 | smoke outlet aperture 5151 |
| liquid injection hole 5152 | sensing opening 5153 | sensing tube 516 |
| sensing passage 5161 | air inlet hole 517 | first latching groove 518 |
| second latching groove 519 | positioning rib 5111 | sealing element 52 |
| limiting rib 521 | smoke outlet hole 522 | sealing portion 523 |
| sealing protrusion 524 | sensing hole 5241 | mounting groove 525 |
| liquid injection groove 526 | air guiding groove 527 | sensing slot 528 |
| liquid absorbing member 5251 | through hole 5252 | mouthpiece 53 |
| first latching tab 531 | smoke outlet opening 532 | protrusion 533 |
| opening 534 | air inlet opening 535 | guiding plate 536 |
| atomizing assembly 54 | bottom base 541 | second latching tab 5411 |
| abutting edge 5412 | holding groove 5413 | sensing aperture 5414 |
| first electrode opening 5415 | second electrode opening 5416 | air inlet groove 5417 |
| sealing plug 542 | ventilation gap 5420 | sealing plate 5421 |
| sealing column 5422 | sealing rib 5427 | air inlet aperture 5423 |
| first electrode hole 5424 | second electrode hole 5425 | sensing hole 5426 |
| conductive sheet 543 | vent pipe 544 | venting section 5441 |
| sleeve section 5442 | smoke outlet passage 5443 | atomizing chamber 5444 |
| atomizer 545 | heating member 5451 | liquid guiding member 5452 |
| first electrode 546 | second electrode 547 | liquid injection needle 70 |
| battery assembly 60 | battery casing 61 | receiving chamber 611 |
| guiding groove 612 | sensing gap 613 | sensor 6131 |
| decoration plate 614 | notch 615 | battery holder 62 |
| first terminal 621 | second terminal 622 | first magnetic member 623 |

| | | |
|---|---|---|
| sensing groove 624 | sealing ring 625 | battery 63 |
| control board 64 | USB interface 641 | magnetic attraction member 5418 |
| sealing gasket 5446 | vent sealing element 5428 | liquid intake hole 5445 |
| first surface 91 | second surface 92 | third surface 93 |
| fourth surface 94 | fifth surface 95 | sixth surface 96 |
| seventh surface 97 | eighth surface 98 | top surface 910 |
| bottom surface 920 | communication opening 548 | |

DETAILED DESCRIPTION OF PREFERRED EMBODIMENTS

The present disclosure will now be described in detail with reference to the drawings. These drawings are simplified schematic diagrams, which only illustrate the basic structure of the present disclosure in a schematic way, so it only shows the construction related to the present disclosure.

First Embodiment

Please refer to FIG. 1-1, which is a circuit diagram of a charging state indication circuit provided by the present disclosure. As shown in FIG. 1-1, the charging state indicating circuit 100 of the embodiment includes a first color LED D5, a second color LED D4, a diode D3, a first resistor R15, and a second resistor R5.

The anode of the first color LED D5 is electrically connected to the power supply (for example, the 5V power supply shown in the figure) through the first resistor R15, the cathode of the first color LED D5 is electrically connected to the charging state indicating terminal 11 of the charging chip U3; one end of the second resistor R5 is electrically connected to the power supply, the other end of the second resistor R5 is electrically connected to the anode of the diode D3, the cathode of the diode D3 is electrically connected to the charging state indicating terminal 11; the other end of the second resistor R5 is also electrically connected to the anode of the second color LED D4, the cathode of the second color LED D4 is grounded.

The charging chip U3 outputs a low voltage through the charging state indicator terminal 11 during the charging process, the first resistor R15, the first color LED D5, and the charging state indicating terminal 11 of the charging chip U3 form a loop to light up the first color LED D5. The second resistor R5 and the second color LED D4 do not form a loop, and the second color LED D4 is not lit. When the battery assembly is fully charged, the charging chip U3 controls the charging state indicating terminal 11 to be in a high resistance state, and the second resistor R5 and the second color LED D4 form a loop to light the second color LED D4.

The first color displayed when the first color LED D5 is lit is different from the second color displayed when the second color LED D4 is lit. Alternatively, the first color is green and the second color is blue. In actual implementation, the first color and the second color can also be other different colors, which will not be repeated in this embodiment.

Alternatively, as shown in FIG. 1-1, the third power receiving terminal 12 of the charging chip U3 is connected to the power output terminal 15 of the connector J2, and is electrically connected to the external power supply through the connector J2 to receive the current provided by the external power supply. The charging voltage output terminal 10 of the charging chip U3 and the positive electrode of the battery assembly (for example, the battery assembly BAT1 as shown in FIG. 1-1) are used to output the charging voltage to the positive electrode of the battery assembly. In one embodiment, the third power receiving terminal 12 and the charging voltage output terminal 10 are respectively the VIN pin and the BATT pin of the charging chip U3.

Alternatively, as shown in FIG. 1-1, the enable terminal 13 of the charging chip U3 is grounded, and the enable terminal 13 of the charging chip U3 is active at low level. That is, the charging chip U3 works when its enable terminal 13 receives a low level, and stops working when it receives a high level and stops charging the battery assembly.

Alternatively, as shown in FIG. 1-1, the NTC terminal 5 of the charging chip U3 is electrically connected to the power supply through a thermistor R17, and the NTC terminal 5 is also grounded through a resistor R19.

Figures 1, 2:
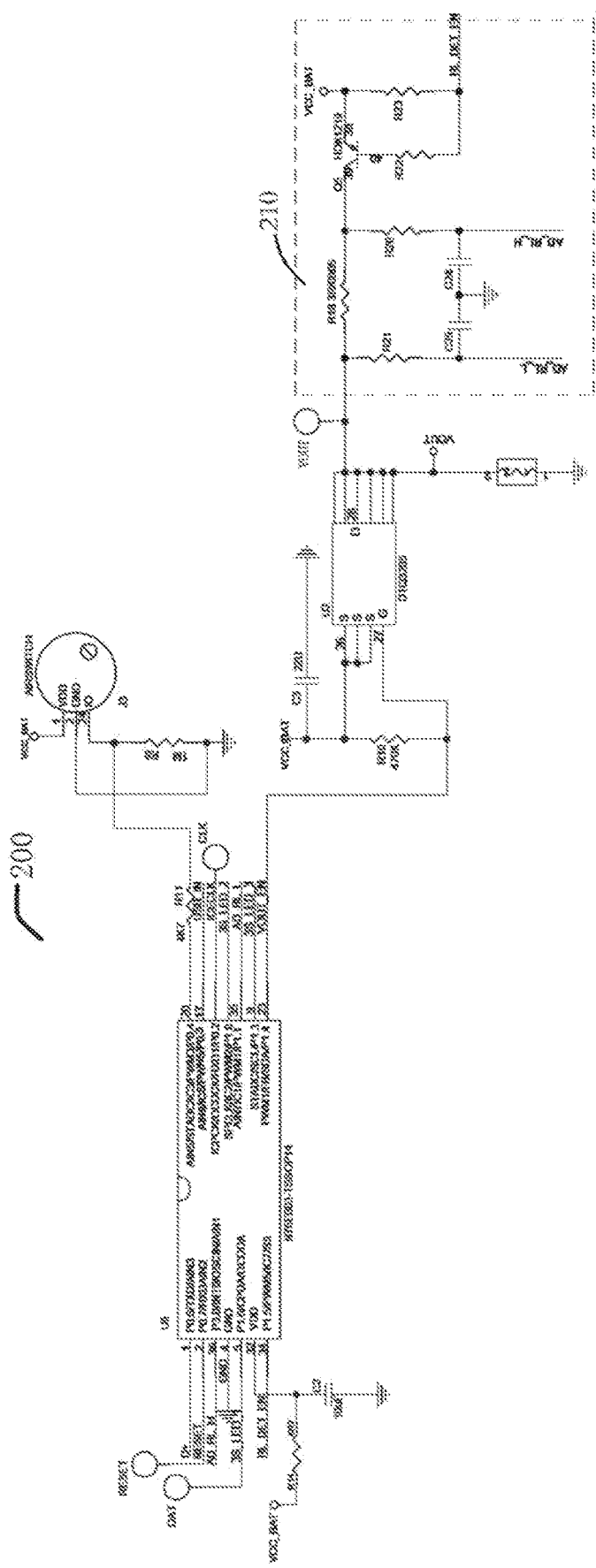

Alternatively, please refer to FIG. 1-1 and FIG. 1-2, the power output terminal 15 of the connector J2 is electrically connected to the universal serial bus (USB) detection pin 17 of the control chip U6 through a resistor R6, the USB detection pin 17 of the control chip U6 is also grounded through a resistor R12. The USB detection pin 17 of the control chip U6 determines whether the connector J2 has a USB plugged into the connector J2 according to the detected voltage.

In summary, the charging state indicator circuit provided by the embodiment of the present disclosure includes a first color LED D5, a second color LED D4, a diode D3, a first resistor R15, and a second resistor R5, wherein the anode of the first color LED D5 is electrically connected to a power supply through the first resistor R15, the cathode of the first color LED D5 is electrically connected to the charging state indicating terminal 11 of the charging chip U3; one end of the second resistor R5 is electrically connected to the power supply, and the other end of the second resistor R5 is electrically connected to the anode of the diode D3, the cathode of the diode D3 is electrically connected to the charging state indicating terminal 11; the other end of the second resistor R5 is also electrically connected to the anode of the second color LED D4, and the cathode of the second color LED D4 is grounded; the charging chip U3 outputs a low voltage through the charging state indicating terminal 11 during the charging process to light up the first color LED D5; the charging chip U3 controls the charging state indicating terminal 11 to be in a high impedance state when the battery assembly is fully charged, so as to light up the second color LED D4. The problem that the green indicator light of the current electronic device is difficult to accurately indicate whether the battery assembly is fully charged is solved; the effect of accurately prompting the charging state of the battery assembly is achieved.

Figures 1, 2, 3:
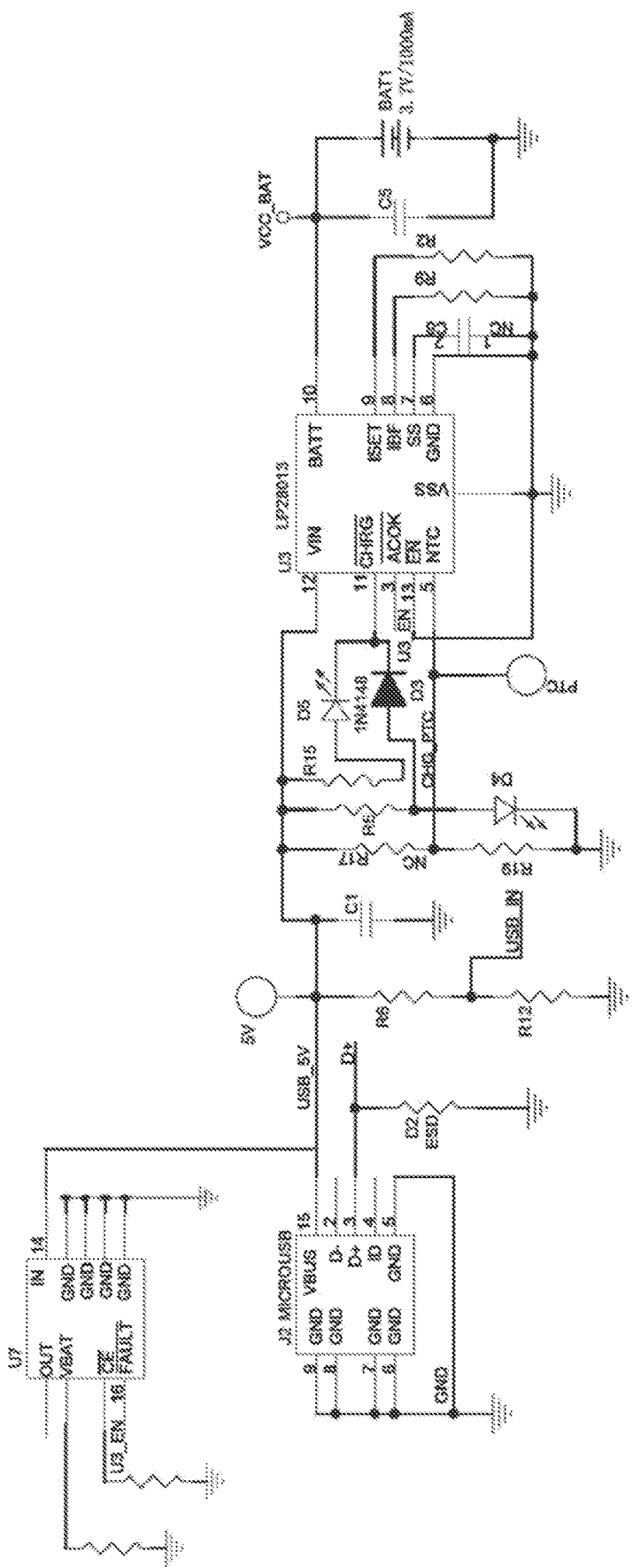
Figures 1, 2, 3, 4:
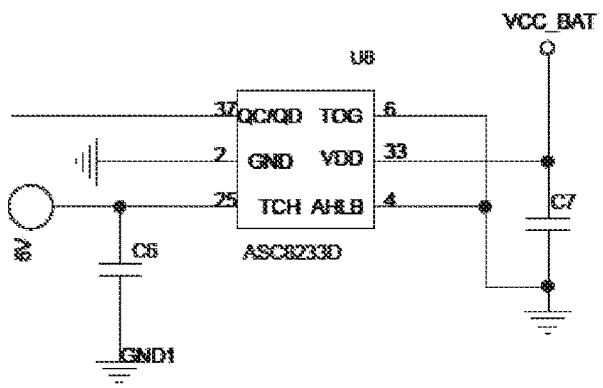

Alternatively, please refer to FIG. 1-3, in order to avoid damage to the charging state indicator circuit due to the charging voltage provided by the external power supply being higher than the limit charging voltage of the charging state indicator circuit, the charging state indication circuit also includes an overvoltage protection chip U7 and a connector J2, the first power receiving terminal 14 of the overvoltage protection chip U7 is connected to the power output terminal 15 of the connector J2, the state indicating terminal 16 of the overvoltage protection chip U7 is electrically connected to the enabling terminal 13 of the charging chip U3, the voltage detection terminal 18 of the overvoltage protection chip U7 is grounded through a third resistor R30, wherein when the voltage on the voltage detection terminal 18 of the overvoltage protection chip U7 reaches the reference voltage, it indicates that the charging voltage provided by the external power supply is higher than the limit charging voltage of the charging state indicator circuit; the state indicating terminal 16 outputs a high level to the enable terminal 13 of the charging chip U3 to stop the charging chip U3 from working, and the state indicating terminal 16 is active at a low level; when the voltage on the voltage detection terminal 18 of the overvoltage protection chip U7 is lower than the reference voltage, it outputs a low level through the state indicating terminal 16 to make the charging chip U3 work.

Alternatively, the state indicating terminal 16 of the overvoltage protection chip U7 is grounded through a third color LED (not shown in the figure). When the voltage on the voltage detection terminal 18 of the overvoltage protection chip U7 reaches the reference voltage, the third color LED is lighted up by outputting a high level from the state indicating terminal 16, to prompt the user that the charging voltage of the external power supply is too large to replace the external power supply that provides electrical energy to the charging state indicating circuit.

Alternatively, the first color LED D5 and/or the second color LED D4 and/or the third color LED are packaged in a lamp group. The third color of the third color LED is different from the first color and the second color, for example, the third color may be red.

Please refer to FIG. 1-2, which shows the voltage output circuit 200 in the charging state indication circuit. The voltage output circuit 200 includes a control chip U6 and a buck switch chip U2.

Specifically, the control chip U6 includes a first control signal input terminal 20 and a modulation signal output terminal 23, The first control signal input terminal 20 of the control chip U6 is electrically connected to the first control signal output terminal 24 of the suction detection element J3, the ground terminal GND of the suction detection element J3 is grounded, the power receiving terminal VDD of the suction detection element J3 receives the system power supply voltage VCC_BAT. Among them, the suction detection element J3 may be a detection element such as a microphone, an airflow sensor, an air pressure sensor, etc., which can be used to detect whether the user is sucking.

Specifically, the buck switch chip U2 includes a first conducting terminal 26, a first control terminal 27, and a second conducting terminal 28, the first conducting terminal 26 of the buck switch chip U2 receives the system power supply voltage VCC_BAT, the first control terminal 27 of the buck switch chip U2 is connected to the modulation signal output terminal 23 of the control chip U6.

In one embodiment, the control chip U6 can be, but is not limited to, an integrated chip with a model of N76E003-TSSOP14. When the control chip U6 is the N76E003-TSSOP14 integrated chip, the first control signal input terminal 20 is the AIN5/STADC/IC3/PWM3/P0.4 pin, the modulation signal output terminal 23 is the PWM1/FB/SDA/P1.4 pin, the second control signal input terminal is AIN6/IC5/PWN5/P0.3.

In one embodiment, the buck switch chip U2 can be, but is not limited to, a PMOS (positive channel metal oxide semiconductor) integrated chip with a model of DTQ3205. When the buck switch chip U2 is a PMOS with a model of DTQ3205, the first conducting terminal 26 of the buck switch chip U2 is the source, the second conducting terminal 28 is the drain, the first control terminal 27 is the gate. In other embodiments, the buck switch chip U2 can also be other types or other types of integrated chips, such as AOS7423, which is not limited in this embodiment.

Specifically, when the suction detection element J3 detects a suction signal, it outputs an effective level through the first control signal output terminal 24 (set by the system developer, it can be high or low); the control chip U6 controls its modulation signal output terminal 23 to output a pulse modulation signal to the first control terminal 27 of the buck switch chip U2 according to the received effective level; therefore, when the first control terminal 27 of the buck switch chip U2 receives a pulse width modulation signal of an effective level (for example, the effective level of the PMOS is low), control the conduction between the first conducting terminal 26 and the second conducting terminal 28, so that the second conducting terminal 28 outputs the driving voltage VOUT whose voltage value is less than the voltage value of the system power supply voltage VCC_BAT.

When the above-mentioned charging state indication circuit is applied to an electronic cigarette, the electronic cigarette only provides a sensor for the user to light up the cigarette. Alternatively, the electronic cigarette can also provide a touch panel for the user to perform a cigarette lighter operation. The specific implementation can be: the control chip U6 further includes a second control signal input terminal (not shown in the figure).

Please refer to FIG. 1-4, the second control signal input terminal of the control chip U6 is connected to the second control signal output terminal 37 of the touch sensor chip U8, the touch input pin 25 of the touch sensor chip U8 is connected to a touch pad (not shown in the figure), the touch input pin 25 of the touch sensor chip U8 is also grounded through the filter capacitor C6, the power input terminal 33 of the touch sensor chip U8 receives the system power supply voltage VCC_BAT and is grounded through the filter capacitor C7.

When the touch input pin 25 of the touch sensor chip U8 detects a touch signal, the effective level is output through the second control signal output terminal 37 (set by the system developer, it can be high or low Level) to the control chip U6, so that the control chip U6 controls its modulation signal output terminal 23 to output a pulse modulation signal to the first control terminal 27 of the buck switch chip U2 according to the received effective level. Therefore, when the first control terminal 27 of the buck switch chip U2 receives a pulse width modulation signal of an effective level (for example, the effective level of the PMOS is low), it controls the first conducting terminal 26 and the second conducting terminal. 28 is turned on, so that the second conducting terminal 28 outputs the driving voltage VOUT whose voltage value is less than the voltage value of the system power supply voltage VCC_BAT.

Alternatively, the reset signal input terminal of the control chip U6 is electrically connected to the reset button, when the control chip U6 is the N76E003-TSSOP14 integrated chip, the reset signal input terminal of the control chip U6 can be the P0.7/RXDAIN2 pin.

In one embodiment, please refer to FIG. 1-2, the first control signal input terminal 20 of the control chip U6 is electrically connected to the first control signal output terminal 24 of the suction detection element J3 through the first current limiting resistor R11, The fourth power receiving terminal VDD of the suction detecting element J3 receives the system power supply voltage VCC_BAT; the first control signal output terminal 24 of the suction detecting element J3 is grounded through the fourth current limiting resistor R8.

In one embodiment, the second control signal input terminal of the control chip U6 is connected to the second control signal output terminal 37 of the touch sensor chip U8 through a second current limiting resistor (not shown in the figure).

In one embodiment, the first conducting terminal 26 of the buck switch chip U2 is connected to the modulation signal output terminal 23 of the control chip U6 through the third current limiting resistor R10; the first conducting terminal 26 is also grounded through the filter capacitor C3.

In one embodiment, the control chip U6 further includes a fifth power receiving terminal 32 and a ground terminal. The fifth power receiving terminal 32 of the control chip U6 is grounded through the filter capacitor C2 and receives the system power supply voltage VCC_BAT through the fifth current limiting resistor R14. Alternatively, the fifth power receiving terminal 32 and the ground terminal of the control chip U6 may be, but not limited to, the VDD pin and the GND pin of the N76E003-TSSOP14 integrated chip, respectively.

In one embodiment, the second conducting terminal 28 of the buck switch chip U2 is connected to a heating wire (not shown in the figure), and the heating wire is driven by the output driving voltage VOUT to generate heat, so as to realize the atomization function.

Alternatively, the voltage output circuit provided by the present application includes the above-mentioned suction detection element J3 and/or the touch sensor chip U8.

In addition, in this embodiment, the first current-limiting resistor R11, the second current-limiting resistor, and the third current-limiting resistor R10 can be used for current-limiting protection to prevent circuit damage and enhance the stability of the voltage output circuit 200.

Alternatively, the control chip U6 further includes a second enable signal output terminal 34, a first current receiving terminal 35, and a second current receiving terminal 36. The voltage output circuit also includes a resistance detection circuit 210, which controls the second enable signal output terminal 34 of the chip U6. The second enable signal output terminal 34 is connected to the resistance detection circuit 210.

In one embodiment, the second enable signal output terminal 34, the first current receiving terminal 35, and the second current receiving terminal 36 can be, but not limited to, P1.5/PWM5/IC7/SS pin, AIN7IC1/PWM1/P1.1 pin, P3.0/INTO/OSCIN/AIN1 pin of N76E003-TSSOP14 integrated chip, respectively.

The resistance detection circuit 210 includes a sixth current-limiting resistor R23, a seventh current-limiting resistor R22, a first detection resistor R18, a second detection resistor R21, a third detection resistor R20, a filter capacitor C25, a filter capacitor C24, and a second switching element Q5.

The fifth conducting terminal 38 of the second switching element Q5 receives the system power supply voltage VCC_BAT, and is connected to the second enable signal output terminal 34 of the control chip U6 through the sixth current limiting resistor R23; the third control terminal 40 of the second switching element Q5 is connected to the second enable signal output terminal 34 of the control chip U6 through the seventh current limiting resistor R22; the sixth conducting terminal 39 of the second switching element Q5 is connected to the second conducting terminal 28 of the buck switch chip U2 through the first detection resistor R18.

One end of the second detection resistor R21 is grounded through the filter capacitor C25, and is connected to the first current receiving terminal 35 of the control chip U6, the other end of the second detection resistor R21 is connected to the second conducting terminal 28 of the buck switch chip U2. One end of the third detection resistor R20 is grounded through the filter capacitor C24, and is connected to the second current receiving terminal 36 of the control chip U6, the other end of the third detection resistor R20 is connected to the sixth conducting terminal 39 of the second switching element Q5.

In one embodiment, the second switching element Q5 may be a PNP transistor, the fifth conducting terminal 38 of the second switching element Q5 is the emitter, and the third control terminal 40 of the second switching element Q5 is the base, the sixth conducting terminal 39 of the second switching element Q5 is the collector. In other embodiments, the second switching element Q5 can also be other types of transistors (such as PMOS transistors) and so on.

The second switching element Q5 is a PNP type transistor as an example for description. Specifically, when neither the first control signal input terminal 20 nor the second control signal input terminal receives an effective level and an atomizer (or heating wire) is installed in the electronic cigarette, the first enable signal output terminal of the control chip U6 outputs a low-level signal, thus, the second switching element Q5 is turned on, and the first current receiving terminal 35 and the second current receiving terminal 36 of the control chip U6 respectively receive the current flowing through the second detection resistor R21 and the third detection resistor R20; and the resistance value of the heating wire is obtained according to the current difference received by the first current receiving terminal 35 and the second current receiving terminal 36.

The voltage output circuit 200 of this embodiment includes a resistance value detection circuit 210, so the resistance value of the heating wire can be obtained according to the current difference output by the resistance value detection circuit 210, so that the output pulse width can be adjusted according to the resistance value of the heating wire The duty cycle of the modulated signal; thus, the voltage value of the driving voltage VOUT output to the heating wire is adjusted, and the flexibility is further enhanced.

In any of the foregoing embodiments, the charging state indicating circuit further includes a motor. Please refer to FIG. 1-5, which is a schematic diagram of a motor connection provided by an embodiment of the present disclosure. The first enable signal output terminal (not shown in the figure) of the control chip U6 is electrically connected to the second control terminal 30 of the first switching element Q11, the third conducting terminal 29 of the first switching element Q11 is grounded, the fourth conducting terminal 18 of the first switching element Q11 is electrically connected to the negative terminal MA− of the motor, the positive terminal MA+ of the motor receives the system power supply voltage VCC_BAT.

When the second control signal input terminal receives the effective level, the first switching element Q11 controls the third conducting terminal 29 and the fourth conducting terminal 18 to be conducted according to the enable signal provided by the first enable signal output terminal of the control chip U6, so that the motor is energized to work, to prompt the user that the touch on the touchpad is effective and to simulate the feel of a physical button.

Alternatively, in the voltage output circuit 200 provided in any of the foregoing embodiments, the second control signal input terminal is electrically connected to the button; the user can light up a cigarette by operating buttons, operating the touchpad, or suction.

In an example of any of the above embodiments, please refer to FIG. 1-6, the charging state indication circuit further includes a battery protection chip U1, the battery protection chip U1 includes a second power receiving terminal 41, a ground terminal 42, and a charging detection terminal. 43. Alternatively, the battery protection chip U1 further includes a heat sinking terminal (not shown in the figure).

Specifically, the second power receiving terminal 41 of the battery protection chip U1 is connected to the positive electrode BAT+ of the battery assembly (for example, the rechargeable battery BAT shown in the figure), the ground terminal 42 of the battery protection chip U1 is connected to the negative electrode BAT− of the battery assembly, the heat sinking terminal of the battery protection chip U1 is connected to the ground terminal 42 of the battery protection chip U1, and the charge detection terminal 43 of the battery protection chip U1 is grounded. The heat sinking terminal of the battery protection chip U1 is used to reduce the temperature of the battery protection chip U1 to avoid high temperature burnout. The heat sinking terminal of the battery protection chip U1 is connected to the ground terminal 42 of the battery protection chip U1, which increases the grounding area of the battery protection chip U1, thereby increasing the overcurrent capability of the voltage output circuit 200.

Specifically, the battery protection chip U1 of this embodiment can be used to prevent overcharge or overdischarge of the battery assembly, and the ground terminal 42 of the battery protection chip U1 is connected to the negative electrode BAT− of the battery assembly. The charge detection terminal 43 of the battery protection chip U1 is grounded, and the negative pole BAT− of the battery assembly is not directly grounded. The battery protection chip U1 is arranged between the negative pole BAT− of the battery assembly and the system ground. When the battery assembly needs to be charged or discharged, the negative electrode BAT− of the battery assembly needs to be connected to the ground through the conductive battery protection chip U1; therefore, the battery protection chip U1 in the voltage output circuit 200 can detect the current or voltage on its own pins or components, determine whether the circuit state is in overcharge or overdischarge state, and then disconnect the negative pole BAT− of the battery assembly with the system ground in the overcharge or overdischarge state, so as to protect the battery assembly.

In one embodiment, the second power receiving terminal 41 of the battery protection chip U1 is connected to the first terminal of the filter capacitor C4, the second end of the filter capacitor C4 is connected to the negative electrode BAT− of the battery assembly. The filter capacitor C4 can be used to filter the system power supply voltage VCC_BAT output by the positive electrode BAT+ of the battery assembly.

In one embodiment, the model of the battery protection chip U1 is XB6006A2. Please refer to FIG. 1-6, the second power receiving terminal 41 of the battery protection chip U1 is the VDD terminal, the ground terminal 42 is the GND terminal, and the charging detection terminal 43 is the VM terminal.

The electronic cigarette of the present disclosure can automatically disconnect the connection between the battery assembly and the charging chip U3 or the discharge circuit through the battery protection chip U1, preventing the occurrence of overcharge or overdischarge of the battery assembly, thereby protecting the battery assembly and e-cigarette.

An embodiment of the present disclosure also provides an electronic device, which includes the charging state indication circuit involved in any of the foregoing embodiments. The electronic device can be any device with rechargeable battery components, such as electronic cigarettes, tablet computers, mobile phones, and so on.

Second Embodiment

Referring to FIGS. 2, 3, 4 and 19, the second embodiment of the present disclosure provides an electronic cigarette. The electronic cigarette includes a cartridge 50 and a battery assembly 60 electrically connected to the cartridge 50. The cartridge 50 includes a cartridge casing 51 with a liquid storage chamber 510 therein, a sealing element 52 used for sealing the liquid storage chamber 510, a mouthpiece 53 installed at one end of the cartridge casing 51, and an atomizing assembly 54 installed at the other end of the cartridge casing 51 opposite to the mouthpiece 53. In use, the atomizing assembly 54 heats the e-liquid stored in the liquid storage chamber 510 under the electric driving of the battery assembly 60, so that the e-liquid is heated to generate smoke, and the smoke can be inhaled by the user.

Figures 1, 2, 3, 4, 5:
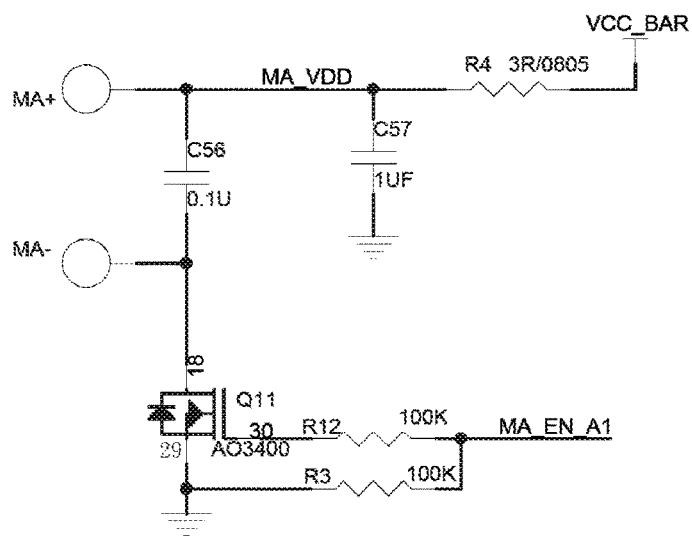
Figures 1, 2, 3, 4, 5, 6:
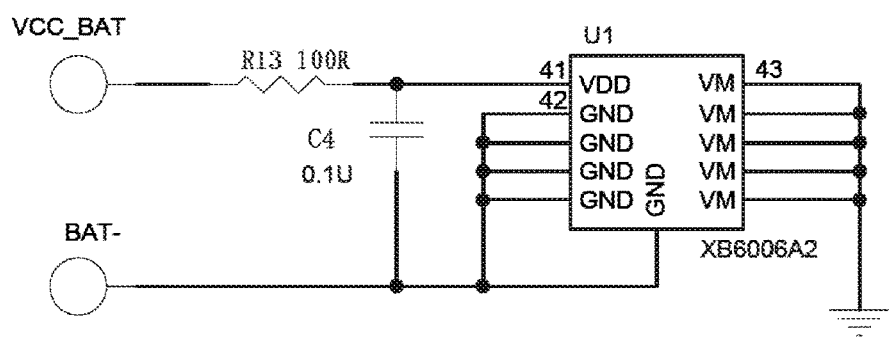
Figures 1, 2:
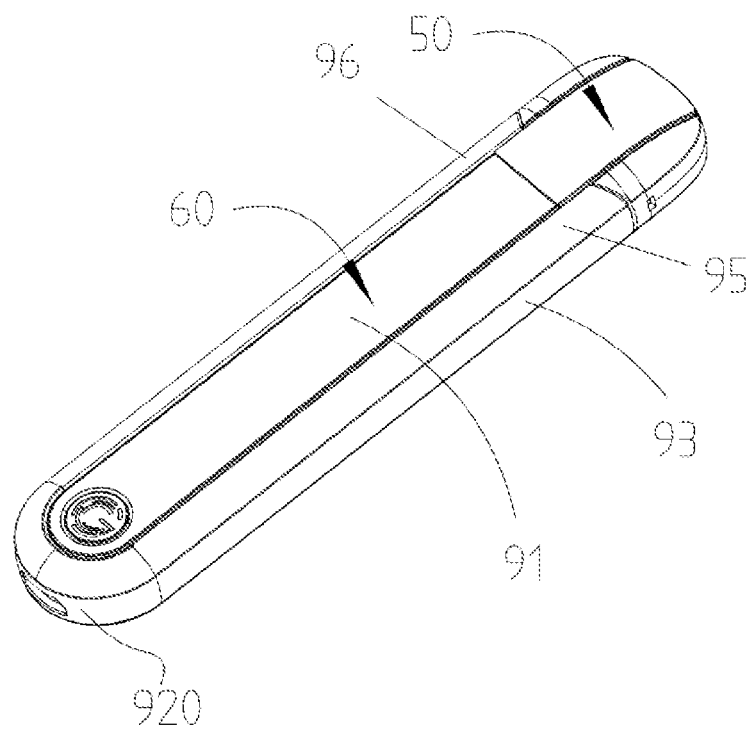
Figure 2:
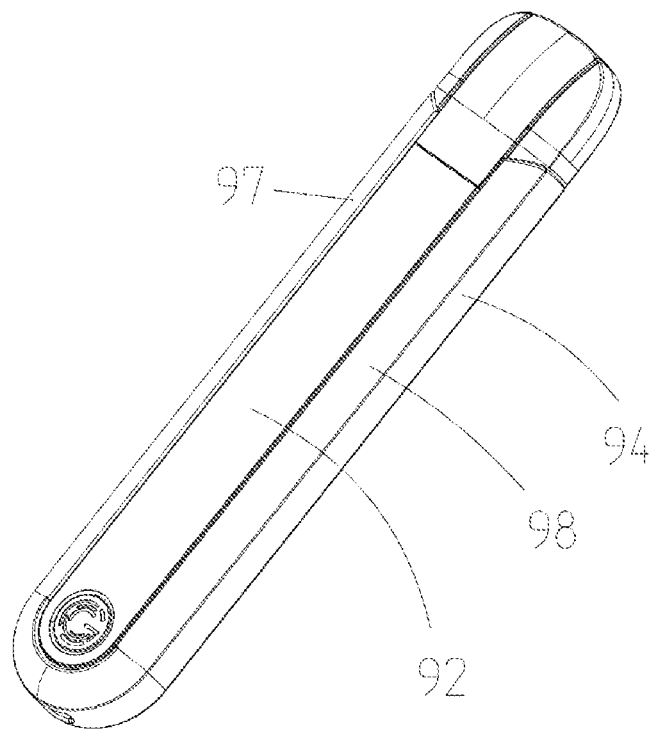
Figures 2, 3:
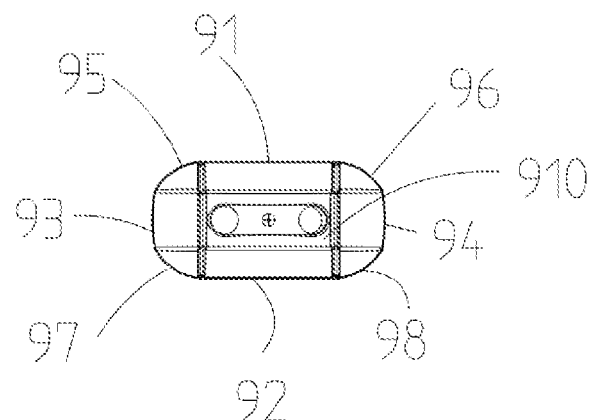
Figure 3:
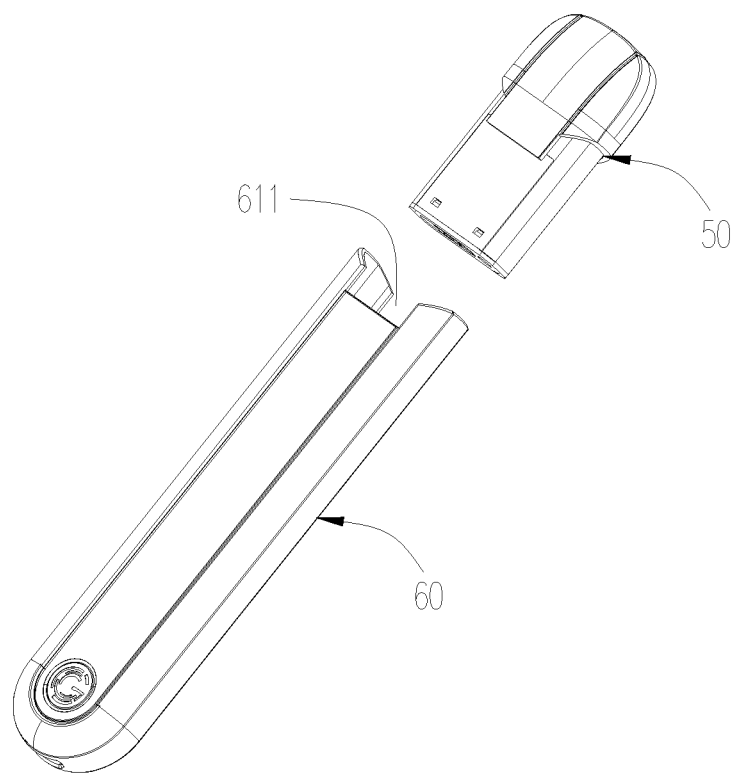
Figure 4:
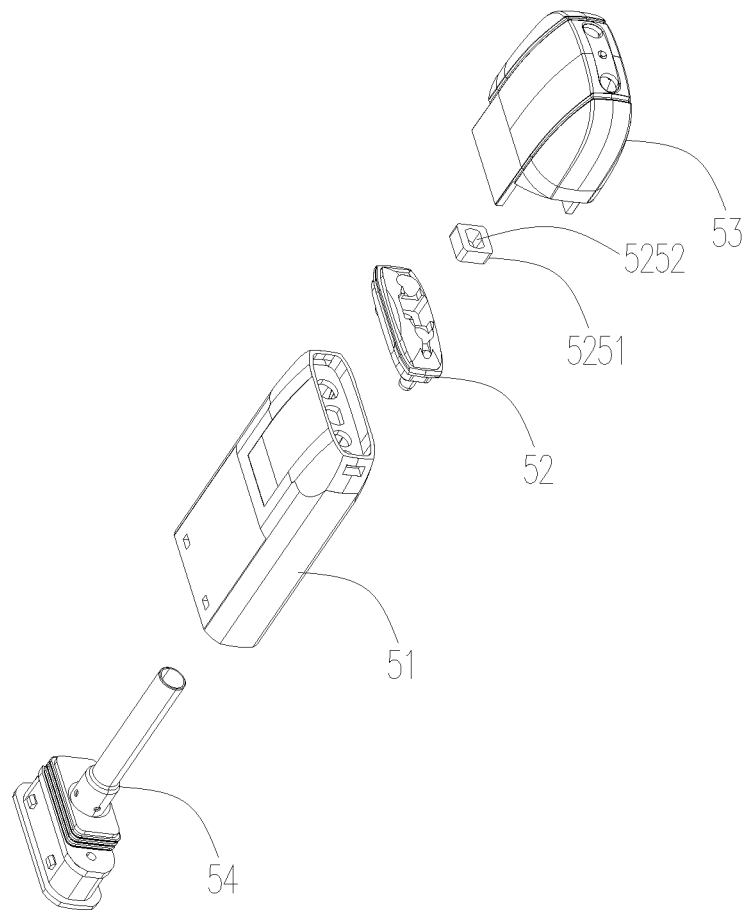
Figure 5:
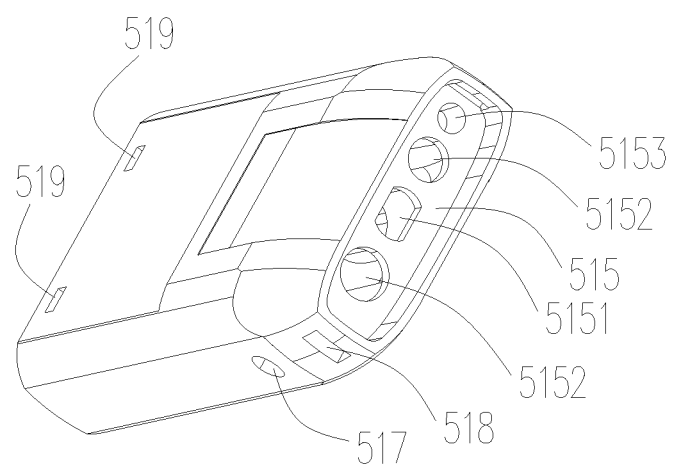
Figure 6:
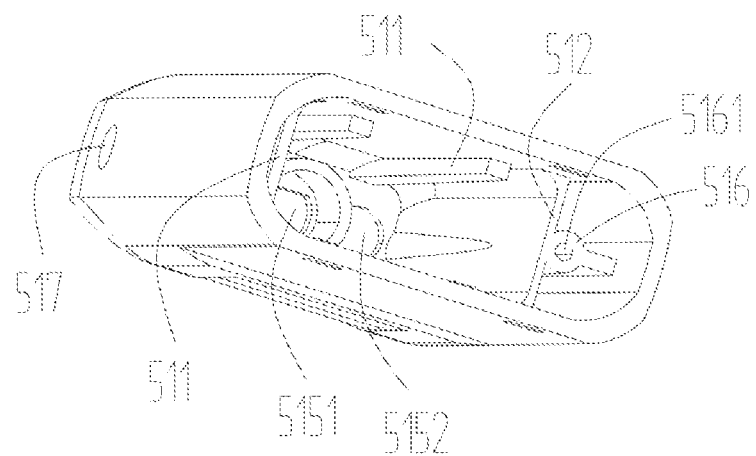
Figure 7:
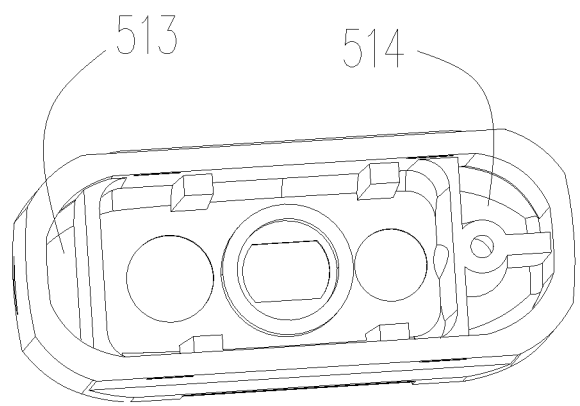
FIG. 7 is a perspective view of the cartridge casing in the cartridge shown in FIG. 4 from a further viewing angle.
Figure 8:
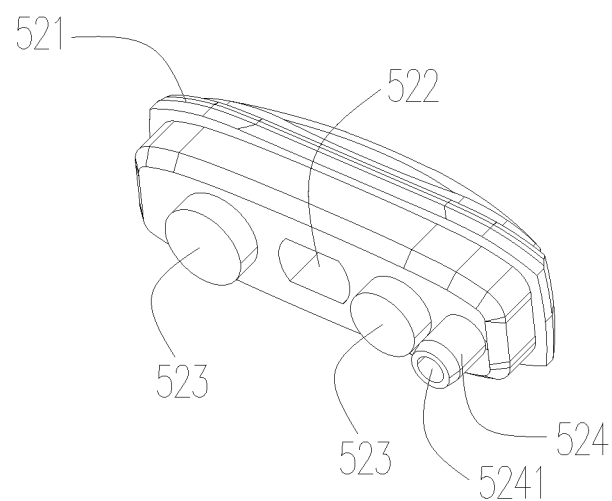
FIG. 8 is a perspective view of the sealing element of the cartridge shown in FIG. 4.
Figure 9:
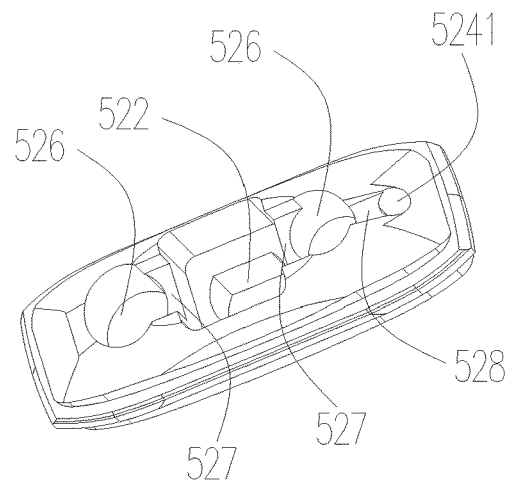
FIG. 9 is a perspective view of the sealing element of the cartridge shown in FIG. 4 from another viewing angle.
Figure 10:
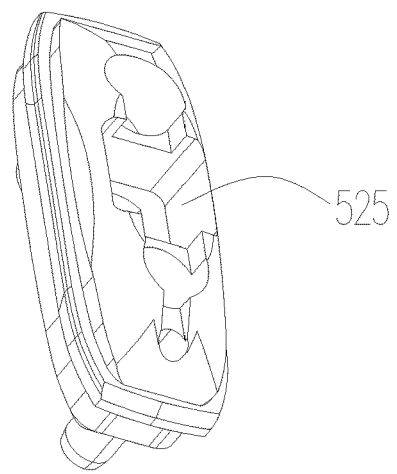
FIG. 10 is a perspective view of the sealing element of the cartridge shown in FIG. 4 from a further viewing angle.

Please refer to FIGS. 5, 6, and 7, the cartridge casing 51 substantially has a hollow cylindrical structure with an opening at the lower end. A first partition plate 511 and a second partition plate 512 are installed in the cavity of the cartridge casing 51 and disposed opposite to each other. The first partition plate 511 and the second partition plate 512 are arranged along the axial direction of the cartridge casing 51. The upper end of each of the first partition plate 511 and the second partition plate 512 is connected to the upper end of the cartridge casing 51. The liquid storage chamber 510 is constituted by a cavity enclosed between the first partition plate 511, the second partition plate 512 and the cartridge casing 51. The space enclosed between the first partition plate 511 and the cartridge casing 51 forms an air inlet chamber 513. The space enclosed between the second partition plate 512 and the cartridge casing 51 forms a sensing chamber 514. The air inlet chamber 513 and the sensing chamber 514 are respectively isolated from the liquid storage chamber 510 by the first partition plate 511 and the second partition plate 512, and are respectively located at two opposite sides of the liquid storage chamber 510. In addition, the cartridge casing 51 is made of a transparent or translucent material, so that the user can observe the amount of e-liquid in the liquid storage chamber 510 through the cartridge casing 51, which is convenient for the user to inject the liquid in time or to replace the cartridge 50 in time. In this embodiment, the material of the cartridge casing 51 is transparent or translucent plastic.

The upper end surface of the cartridge casing 51 is recessed downward to form a receiving groove 515. A smoke outlet aperture 5151, a liquid injection hole 5152 and a sensing opening 5153 are provided in the bottom wall of the receiving groove 515. The smoke outlet aperture 5151 is defined at the center of the bottom wall of the receiving groove 515. There are two liquid injection holes 5152, and the two liquid injection holes 5152 are symmetrically arranged with respect to the smoke outlet aperture 5151 at two sides of the smoke outlet aperture 5151. The liquid injection hole 5152 is in communication with the liquid storage chamber 510. It can be understood that, the two liquid injection holes 5152 are symmetrically arranged with respect to the axis of the cartridge 50. A sensing tube 516 is installed in the sensing chamber 514 along the axial direction of the cartridge casing 51. The upper end of the sensing tube 516 is connected to the upper end of the cartridge casing 51, and the lower end surface of the sensing tube 516 is flush with the lower end surface of the second partition plate 512. A sensing passage 5161 is defined in the sensing tube 516 along the axial direction of the cartridge casing 51, the lower end of the sensing passage 5161 extends through the lower end surface of the sensing tube 516, and the upper end of the sensing passage 5161 is aligned with the sensing opening 5153. In this embodiment, the cartridge casing 51, the first partition plate 511, the second partition plate 512 and the sensing tube 516 are integrally formed to facilitate production. In order to facilitate the sensing tube 516 to be integrally formed with the cartridge casing 51, the first partition plate 511 and the second partition plate 512, a reinforcing rib (not labelled) is provided between the sensing tube 516 and the cartridge casing 51. It can be understood that, in other embodiments not shown, the sensing tube 516 can be omitted, and the sensing chamber 514 is used as the sensing passage 5161.

The side wall of the cartridge casing 51 adjacent to the first partition plate 511 is provided with an air inlet hole 517. That is, the side wall of the cartridge casing 51 opposite to the first partition plate 511 is defined with an air inlet hole 517. The air inlet hole 517 is in communication with the outside atmosphere and the air inlet chamber 513.

Please refer to FIGS. 8, 9, 10 and 19, the sealing element 52 substantially has a block structure. The sealing element 52 matches with the receiving groove 515 and is installed in the receiving groove 515. The outer circumferential surface of the sealing element 52 is provided with a limiting rib 521 protruding outwards. When the sealing element 52 is installed in the receiving groove 515, the limiting rib 521 resists against the upper end surface of the cartridge casing 10, thereby limiting the sealing element 52. At the same time, the user can judge whether the sealing element 52 is installed in place by noticing whether the limiting rib 521 resists against the upper end surface of the cartridge casing 10, thereby facilitating the installation of the sealing element 52. The portion of the sealing element 52 located below the limiting rib 521 is received in the receiving groove 515.

The lower end surface of the sealing element 52 is provided with a smoke outlet hole 522, and the smoke outlet hole 522 is aligned with the smoke outlet aperture 5151. A sealing portion 523 and a sealing protrusion 524 are also protruded from on the lower end surface of the sealing element 52. There are two sealing portions 523, and each sealing portion 523 is engaged with one of the liquid injection hole 5152. The sealing protrusion 524 is engaged with the sensing opening 5153 and defined with a sensing hole 5241. One end of the sensing hole 5241 extends through the lower end surface of the sealing protrusion 524, the other end of the sensing hole 5241 extends through the upper end surface of the sealing element 52. When the sealing element 52 is installed in the receiving groove 515, the smoke outlet hole 522 is in communication with the smoke outlet aperture 5151, the sealing portion 523 is inserted into the liquid injection hole 5152 to seal the liquid injection hole 5152 so that the e-liquid in the liquid storage chamber 510 is sealed, and at the same time, the sealing protrusion 524 is inserted into the sensing opening 5153, and the sensing hole 5241 is in communication with the sensing passage 5161. The arrangement of inserting the sealing protrusion 524 into the sensing opening 5153 can prevent the airflow in the sensing passage 5161 from leaking through the gap between the sealing protrusion 524 and the sensing opening 5153. In addition, the sealing portion 523 and the sealing protrusion 524 are protruded downwards, which has a guiding and positioning function when the sealing element 52 and the receiving groove 515 are assembled.

The upper end surface of the sealing element 52 is recessed downward to form a mounting groove 525. The mounting groove 525 is in communication with the smoke outlet hole 522. Specifically, the smoke outlet hole 522 extends through the bottom wall of the mounting groove 525. The upper end surface of the sealing element 52 is provided with two liquid injection grooves 526 located at two sides of the mounting groove 525, respectively. Each liquid injection groove 526 is aligned with one of the sealing portions 523. The upper end surface of the sealing element 52 is provided with an air guiding groove 527 located between each liquid injection groove 526 and the mounting groove 525. One side of the air guiding groove 527 is in communication with the mounting groove 525, and the other side of the air guiding groove 527 is in communication with the corresponding liquid injection groove 526. In addition, the upper end surface of the sealing element 52 is provided with a sensing slot 528 located between the sensing hole 5241 and a liquid injection groove 526 adjacent to the sensing hole 5241. One side of the sensing slot 528 is in communication with the liquid injection groove 526, and the other side of the sensing slot 528 is in communication with the sensing hole 5241.

In addition, a liquid absorbing member 5251 is installed in the mounting groove 525. The liquid absorbing member 5251 matches with the mounting groove 525. A through hole 5252 is provided in the liquid absorbing member 5251. The lower end of the through hole 5252 extends through the lower end surface of the liquid absorbing member 5251 and is in communication with the smoke outlet hole 522. The upper end of the through hole 5252 extends through the upper end surface of the liquid absorbing member 5251. The liquid absorbing member 5251 has the ability of absorbing e-liquid and is used for absorbing the large liquid particles in the smoke and the condensate after the smoke is condensed. In the embodiment, the liquid absorbing member 5251 is a sponge. It can be understood that, the liquid absorbing member 5251 can also be made of fiber rope, cotton, porous ceramics, porous graphite, foamed metal, etc., which is not limited here.

Figure 11:
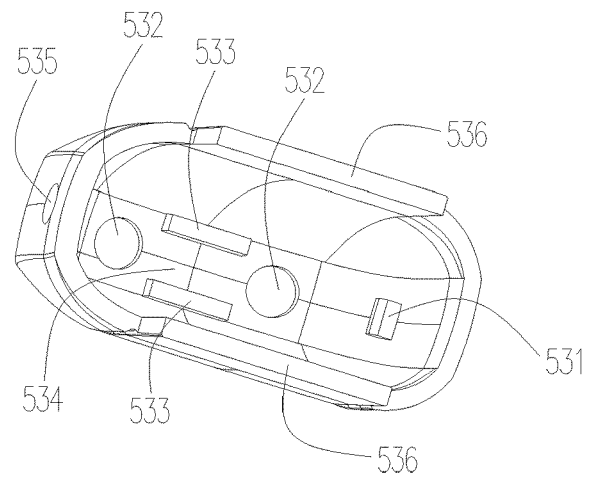
FIG. 11 is a perspective view of the mouthpiece of the cartridge shown in FIG. 4.
Figure 12:
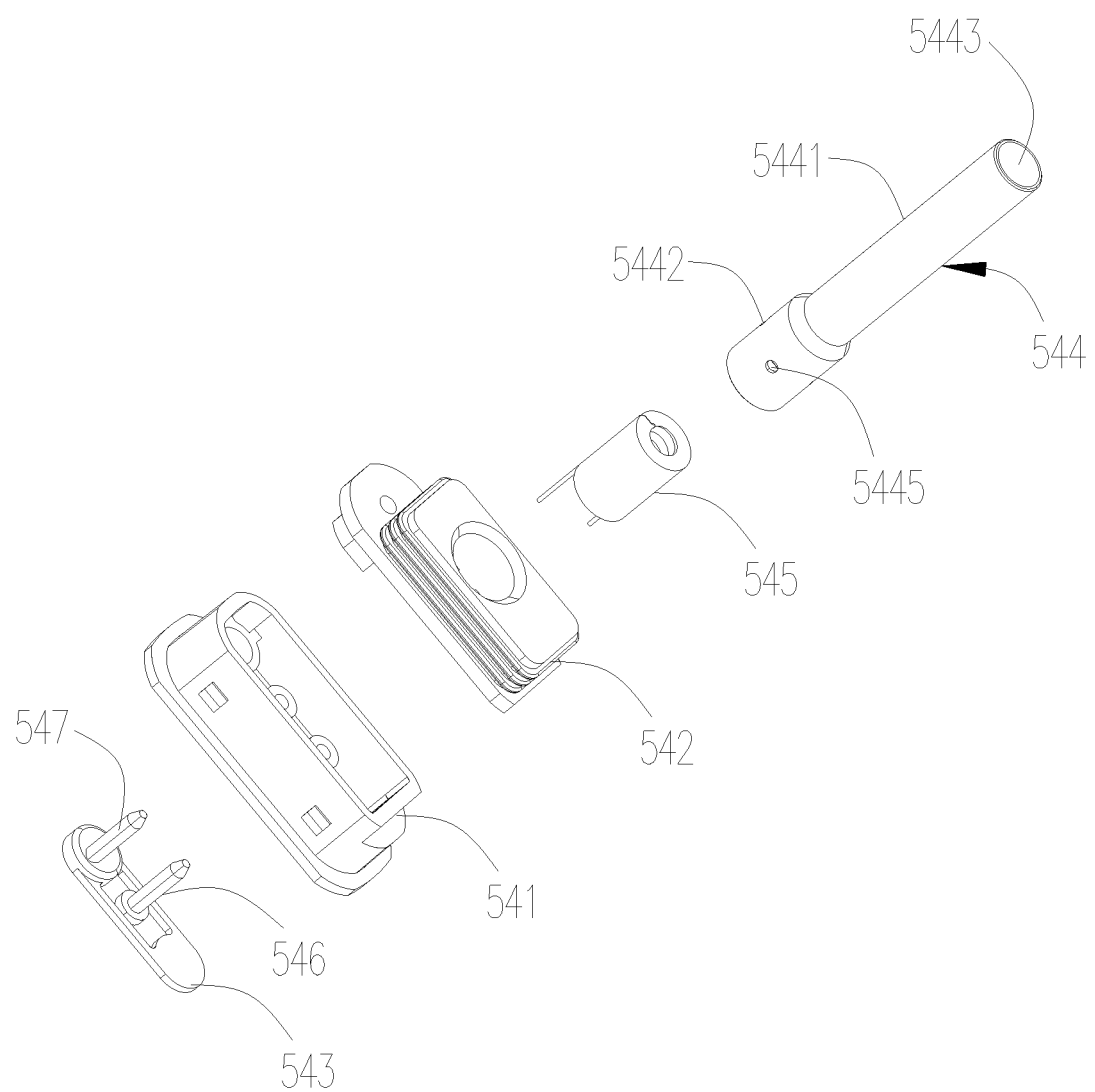
FIG. 12 is an exploded view of the atomizing assembly in the cartridge shown in FIG. 4.
Figure 13:
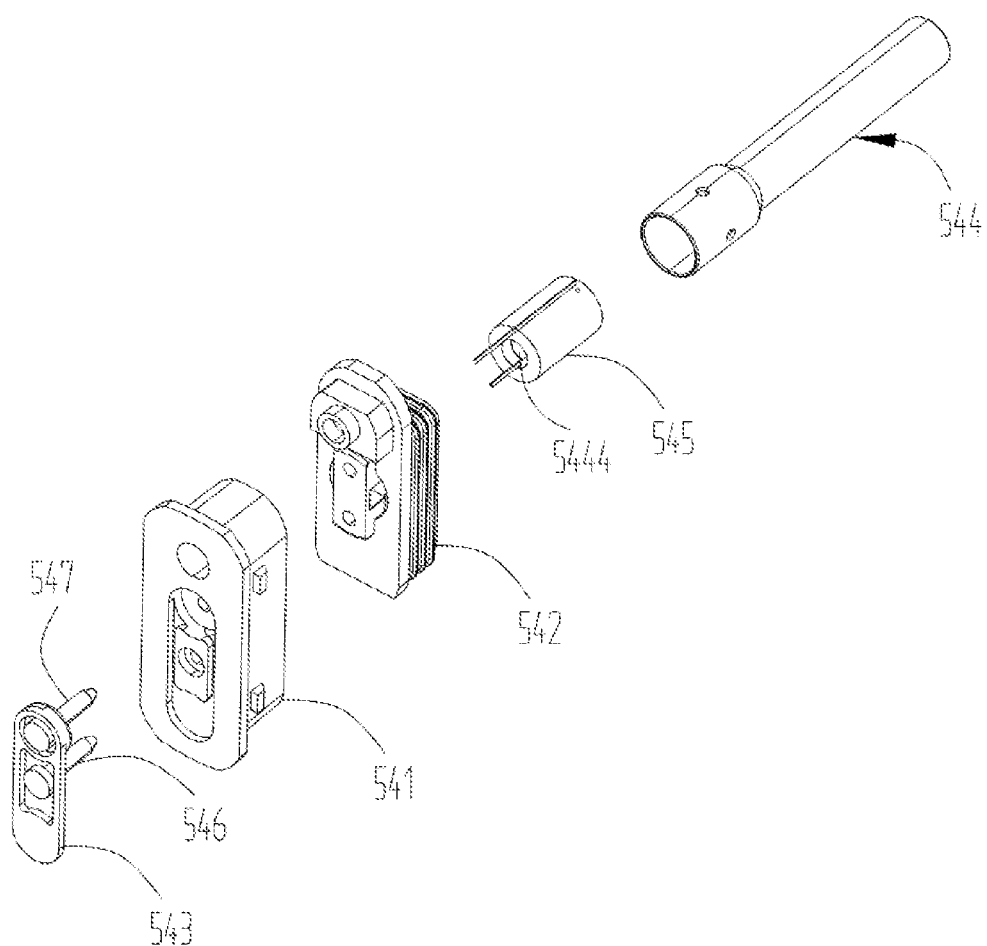
FIG. 13 is an exploded view of the atomizing assembly in the cartridge shown in FIG. 4 from another viewing angle
Figure 19:
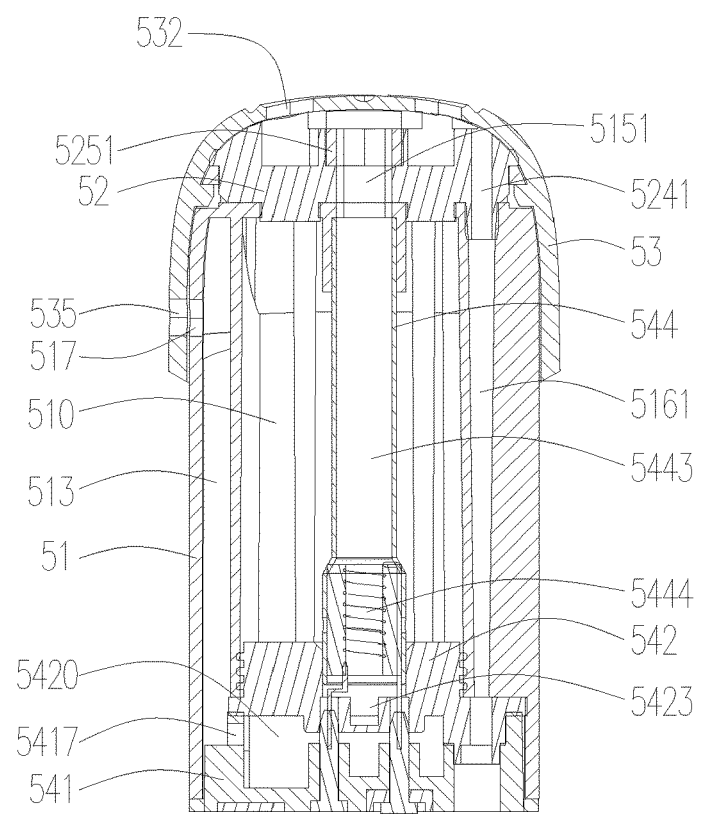
FIG. 19 is a cross-sectional view of the cartridge of the electronic cigarette shown in FIG. 3.

Please refer to FIG. 11 and FIG. 19, the mouthpiece 53 is installed on the upper end of the cartridge casing 51. In this embodiment, the mouthpiece 53 is sleeved on the outside of the upper end of the cartridge casing 51. When the mouthpiece 53 is installed in place, the mouthpiece 53 cannot be removed, to prevent children from disassembling the mouthpiece 53 arbitrarily, then disassembling the sealing element 52 and contacting the liquid in the liquid storage chamber 510. Specifically, the mouthpiece 53 substantially has a hollow cylindrical structure with an opening at the lower end. The outer wall of the cartridge casing 51 is provided with a first latching groove 518, and the inner wall of the mouthpiece 53 is protruded to provide with a first latching tab 531 to be engaged with the first latching groove 518. When the mouthpiece 53 and the cartridge casing 51 are mounted in place, the first latching groove 518 and the first latching tab 531 are engaged with each other, thereby achieving a stable connection relationship between the mouthpiece 53 and the cartridge casing 51. When the mouthpiece 53 and the cartridge casing 51 are mounted in place, the first latching groove 518 and the first latching tab 531 are both covered by the outer wall of the mouthpiece 53, to make the whole cartridge 50 more beautiful. In this embodiment, there are two first latching grooves 518, the two first latching grooves 518 are provided at opposite sides of the cartridge casing 51. Correspondingly, there are two first latching tabs 531, such that the connection between the mouthpiece 53 and the cartridge casing 51 can be made more stable and reliable. It can be understood that, in other embodiments not shown, the first latching tab 531 is provided on the outer wall of the cartridge casing 51, and the first latching groove 518 is defined at the inner wall of the mouthpiece 53. It is understood that, in other embodiments not shown, the mouthpiece 53 and the cartridge casing 51 can also be detachably connected by screw connection, plugging connection, magnetic connection, or the like.

The upper end surface of the mouthpiece 53 is provided with two smoke outlet openings 532. The smoke outlet openings 532 are in communication with the external atmosphere and the inner cavity of the mouthpiece 53. In this embodiment, there are two smoke outlet openings 532, which are symmetrically arranged on two sides of the smoke outlet hole 522. Each smoke outlet opening 532 is aligned with one of the liquid injection groove 526, such that the smoke outlet opening 532 and the smoke outlet hole 522 are staggered, which can effectively prevent the smoke from being directly and quickly drawn out and choking.

The inner surface of the top wall of the mouthpiece 53 is protruded to provide with two protrusions 533 which are disposed opposite to each other. An opening 534 is formed between the two protrusions 533, the opening 534 is in communication with the through hole 5252. When the mouthpiece 53 and the cartridge casing 51 are installed in place, the lower end of the protrusion 533 abuts against the upper end of the liquid absorbing member 5251, thereby fixing the liquid absorbing member 5251. At the same time, the opening 534 is in communication with the air guiding grooves 527, such that the smoke outlet hole 522 is in communication with the smoke outlet openings 532 through the through hole 5252, the opening 534, the air guiding grooves 527 and the liquid injection grooves 526 in sequence. Meanwhile, the sensing hole 5241 is in communication with the smoke outlet opening 532 through the sensing slot 528 and the liquid injection groove 526 in sequence.

In addition, the side wall of the mouthpiece 53 is provided with an air inlet opening 535 aligned with the air inlet hole 517. When the mouthpiece 53 and the cartridge casing 51 are installed in place, the air inlet opening 535 is in communication with the air inlet hole 517.

Refer to FIGS. 12, 13, 18 and 19, the atomizing assembly 54 includes a bottom base 541 installed in the lower end of the cartridge casing 51, a sealing plug 542 installed at the upper end of the bottom base 541, a conductive sheet 543 installed at the lower end of the bottom base 541, a vent pipe 544 installed on the sealing plug 542, an atomizer 545 housed in the lower end of the vent pipe 544, and a first electrode 546 and a second electrode 547 extending through the bottom base 541 into the sealing plug 542.

Figure 14:
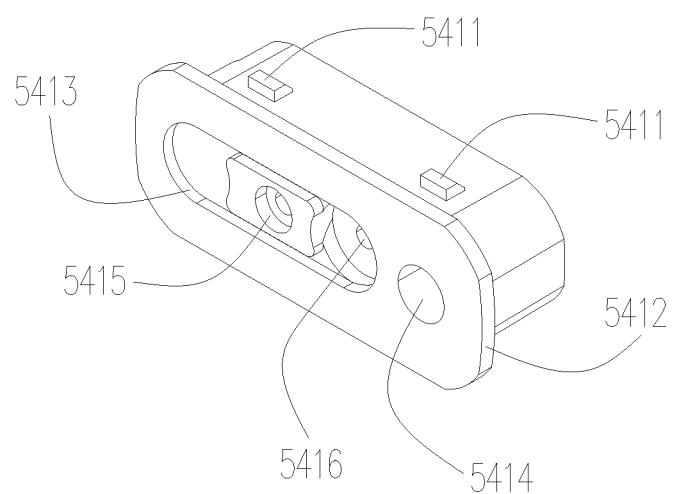
FIG. 14 is a perspective view of the bottom base of the atomizing assembly shown in FIG. 12.
Figure 15:
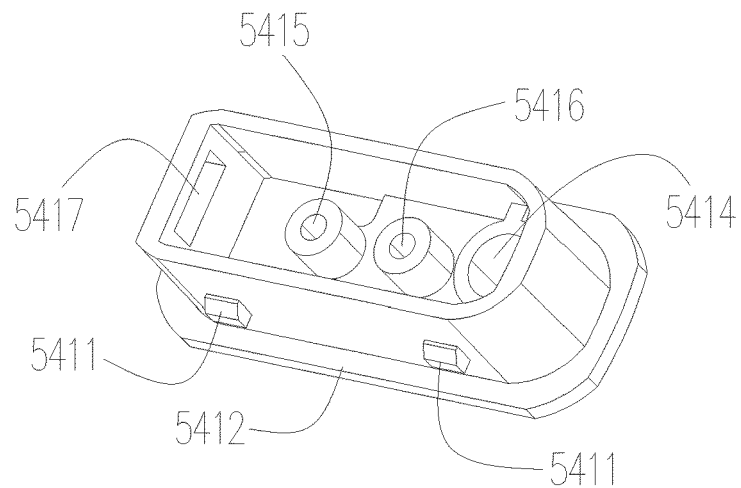
FIG. 15 is a perspective view of the bottom base of the atomizing assembly shown in FIG. 12 from another viewing angle.
Figure 16:
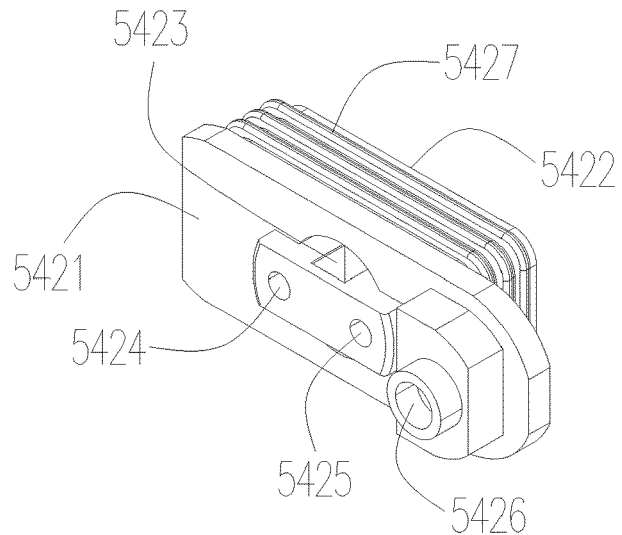
FIG. 16 is a perspective view of the sealing plug of the atomizing assembly shown in FIG. 12.
Figure 17:
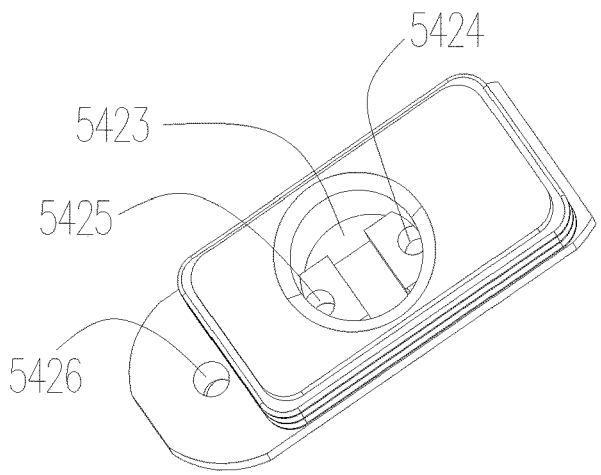
FIG. 17 is a perspective view of the sealing plug of the atomizing assembly shown in FIG. 12 from another viewing angle.
Figure 18:
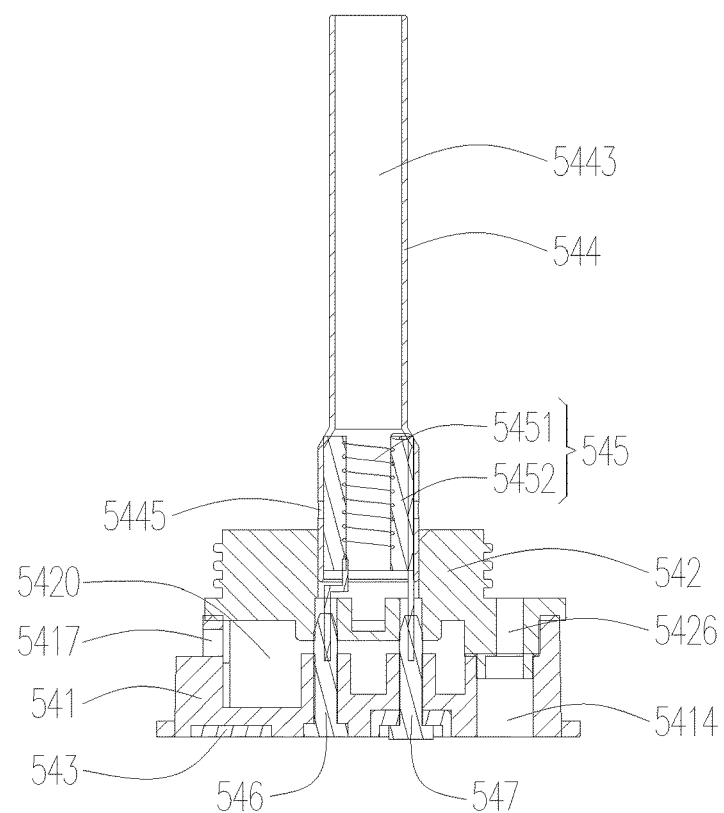
FIG. 18 is a cross-sectional view of the atomizing assembly of the cartridge shown in FIG. 4.

Refer to FIG. 14 and FIG. 15, the bottom base 541 is received in the lower end of the cartridge casing 51. The bottom base 541 has generally a hollow cylindrical structure with an opening at the upper end. A second latching tab 5411 is protruded to provide on the outer wall of the bottom base 541, the side wall of the cartridge casing 51 is provided with a second latching groove 519 to be engaged with the second latching tab 5411. When the bottom base 541 and the cartridge casing 51 are installed in place, the second latching tab 5411 is engaged with the second latching groove 519, so as to achieve a stable connection relationship between the bottom base 541 and the cartridge casing 51, and the second latching tab 5411 and the second latching groove 519 cannot be disassembled, which can prevent children from contacting the liquid in the liquid storage chamber 510 after disassembling the bottom base 541 arbitrarily. It can be understood that, in other embodiments not shown, the second latching tab 5411 is arranged on the side wall of the cartridge casing 51, the second latching groove 519 is defined in the outer wall of the bottom base 541. In this embodiment, the outer peripheral surface of the lower end of the bottom base 541 protrudes outward along the radial direction of the bottom base 541 to form an abutting edge 5412. The upper end surface of the abutting edge 5412 resists the lower end surface of the cartridge casing 51, thereby limiting the position of the bottom base 541. It can be understood that, the atomizing assembly 54 realizes the connection relationship with the cartridge casing 51 through the bottom base 541.

The lower end surface of the bottom base 541 is partially recessed to form a holding groove 5413, and the conductive sheet 543 is placed in the holding groove 5413. The inner bottom wall of the bottom base 541 is protruded to provide with a bump (not labelled), a first connecting post (not labelled) and a second connecting post (not labelled) located in the cavity of the bottom base 541. The bump is provided with a sensing aperture 5414 along the axial direction of the bottom base 541. The first connecting post is provided with a first electrode opening 5415 along the axial direction of the bottom base 541. The second connecting post is provided with a second electrode opening 5416 along the axial direction of the bottom base 541. The sensing aperture 5414, the first electrode opening 5415 and the second electrode opening 5416 are through holes. The bottom base 541 is made of insulating material. In this embodiment, the material of the bottom base 541 is plastic.

In addition, an air inlet groove 5417 is provided at the side wall of the bottom base 541.

Please refer to FIGS. 16-19, the sealing plug 542 is installed on the upper end of the bottom base 541, so that a ventilation gap 5420 is formed between the lower end surface of the sealing plug 542 and the upper end surface of the bottom base 541. The air inlet groove 5417 is in communication with the air inlet chamber 513 and the ventilation gap 5420. Specifically, the sealing plug 542 includes a sealing plate 5421 and a sealing column 5422 protruded on the upper end surface of the sealing plate 5421. The sealing plate 5421 and the sealing column 5422 are integrally formed. One end of the sealing plate 5421 is clamped between the lower end surface of the first partition plate 511 and the upper end surface of the bottom base 541, and the other end of the sealing plate 5421 is clamped between the lower end surface of the sensing tube 516 and the upper end surface of the bottom base 541 for fixing the sealing plug 542. The shape of the sealing column 5422 corresponds to the liquid storage chamber 510, and the sealing column 5422 is installed in the lower end of the liquid storage chamber 510 to seal the e-liquid. In this embodiment, the material of the sealing plug 542 is silicone. It can be understood that, in other embodiments not shown, the material of the sealing plug 542 can also be other sealing materials such as rubber. In addition, positioning ribs 5111 are provided on the inner wall of the cartridge casing 51 along the axial direction of the cartridge casing 51. When the sealing plug 542 is installed in place, the lower end surface of the positioning rib 5111 resists against the upper end surface of the sealing column 5422, so as to limit the installation depth of the sealing plug 542.

In this embodiment, the outer circumferential surface of the sealing column 5422 is provided with sealing ribs 5427 protruding outwards along the radial direction of the sealing column 5422. There are a plurality of sealing ribs 5427, and the sealing ribs 5427 are sequentially spaced and distributed along the axial direction of the sealing column 5422. By providing the sealing ribs 5427, the sealing column 5422 can seal the liquid storage chamber 510 with multiple sealing layers, thereby enhancing the sealing performance and further preventing the leakage of e-liquid.

The center of the upper end surface of the sealing column 5422 is provided with an inserting opening (not labelled) along the axial direction of the sealing plug 542. The bottom of the sealing plate 5421 is provided with an air inlet aperture 5423 in communication with the inserting opening. The air inlet aperture 5423 is in communication with the ventilation gap 5420. The bottom of the sealing plate 5421 is also provided with a first electrode hole 5424 and a second electrode hole 5425. The first electrode hole 5424 is aligned with the first electrode opening 5415, the second electrode hole 5425 is aligned with the second electrode opening 5416. The upper end of the first electrode 546 extends through the first electrode opening 5415 and then is inserted into the first electrode hole 5424; the upper end of the second electrode 547 extends through the second electrode opening 5416 and then is inserted into the second electrode hole 5425. The conductive sheet 543 is sleeved on the outside of the second electrode 547 and is electrically connected to the second electrode 547. The first electrode 546 and the second electrode 547 are insulated by the bottom base 541. The conductive sheet 543 is a conductive body, and the material of the conductive sheet 543 can be metal, for example, iron, copper, nickel, etc., which is not limited here. In this embodiment, the lower end surface of the sealing plate 5421 is provided with a bulge protruding downward along the axial direction of the sealing plate 5421. The first electrode hole 5424 and the second electrode hole 5425 are defined in the lower end surface of the bulge, and both extend upwardly through the sealing plate 5421 along the axial direction of the sealing plug 542 and are in communication with the inserting opening. The arrangement of the bulge increases the depth of the first electrode hole 5424 and the second electrode hole 5425, thereby increasing the installation depth of the first electrode 546 and the second electrode 547, so that the installation of the first electrode 546 and the second electrode 547 is more stable. In addition, the air inlet aperture 5423 is defined in the side wall of the bulge. In this way, a certain suction resistance is increased to prevent the intake airflow from being drawn out quickly and carry less smoke, so that the user has a better experience when inhaling.

In addition, a first connecting column (not labelled) is formed on the lower end surface of the sealing plate 5421 by extending downward along the axial direction of the sealing element 542. The first connecting column is aligned with the sensing aperture 5414, and a sensing hole 5426 is defined in the first connecting column along the axial direction of the sealing element 542. The lower end of the sensing hole 5426 extends through the lower end surface of the first connecting column, the upper end of the sensing hole 5426 extends through the upper end surface of the sealing plate 5421. When the sealing plug 542, the bottom base 541 and the cartridge casing 51 are installed in place, the first connecting column is partially inserted into the sensing aperture 5414, the sensing passage 5161 is in communication with the sensing hole 5426, and further the sensing passage 5161 is in communication with the sensing aperture 5414. The first connecting column seals the sensing aperture 5414 to prevent the airflow in the sensing aperture 5414 from leaking. The first connecting column also serves as an isolation function for separating the ventilation gap 5420 and the sensing aperture 5414 to prevent the airflow in the ventilation gap 5420 and the sensing aperture 5414 from interfering with each other.

Please refer to FIGS. 12, 18 and 19 again, the vent pipe 544 is received in the liquid storage chamber 510, the lower end of the vent pipe 544 is connected with the sealing plug 542, the upper end of the vent pipe 544 is connected to the upper end of the cartridge casing 51. Specifically, the vent pipe 544 is approximately a tubular structure with both ends being opened. The vent pipe 544 includes a venting section 5441 and a sleeve section 5442 that are connected to each other. The inner cavity of the venting section 5441 forms a smoke outlet passage 5443. The inner cavity of the sleeve section 5442 forms a receiving space (not labelled). The diameter of the venting section 5441 is smaller than the diameter of the sleeve section 5442. A connecting pipe (not labelled) is formed on the inner wall of the upper end surface of the cartridge casing 51 by extending downward along the axial direction of the cartridge casing 51. The connecting pipe is aligned with the smoke outlet aperture 5151. One end of the venting section 5441 away from the sleeve section 5442 is connected to the connecting pipe, the smoke outlet passage 5443 is in communication with the smoke outlet aperture 5151. One end of the sleeve section 5442 away from the venting section 5441 is inserted into the inserting opening on the sealing plug 542, the receiving space is in communication with the inserting opening. In addition, the side wall of the sleeve section 5442 is provided with a liquid intake hole 5445. The liquid intake hole 5445 is in communication with the liquid storage chamber 510 and the receiving space. In this embodiment, the venting section 5441 and the sleeve section 5442 are integrally formed. It can be understood that, in other embodiments not shown, the venting section 5441 and the sleeve section 5442 are two independent components, and when in use, they can be connected together.

The atomizer 545 is received in the receiving space. The atomizer 545 includes a heating member 5451 and a liquid guiding member 5452 which are in contact with each other. The heating member 5451 generates heat after being energized, and the liquid guiding member 5452 is capable of absorbing e-liquid. The liquid guiding member 5452 is a hollow structure with both ends opened. The inner cavity of the liquid guiding member 5452 is provided with an atomizing chamber 5444. The liquid guiding member 5452 is made of porous material, and the porous material has air permeability, which can allow air to be discharged. When the liquid guiding member 5452 is in the saturated state, it will not further absorb the e-liquid, thereby sealing the e-liquid in the liquid storage chamber 510; when the heating member 5451 heats the e-liquid absorbed on the liquid guiding member 5452, the liquid guiding member 5452 can further absorb the e-liquid from the liquid storage chamber 510 again. In this embodiment, the liquid guiding member 5452 is wrapped around the heating member 5451 and attached to the inner wall of the sleeve section 5442 corresponding to the liquid intake hole 5445, so that the e-liquid in the liquid storage chamber 510 is absorbed into the atomizing chamber 5444 by the liquid guiding member 5452 through the liquid intake hole 5445. The heating member 5451 has two pins, the upper end of each of the first electrode 546 and the second electrode 547 is provided with an opening, one of the pins is inserted into the opening of the first electrode 546 and then a clamping force is applied to the first electrode 546, so that the opening of the first electrode 546 shrinks inward to clamp the pin. Similarly, the other pin is inserted into the opening of the second electrode 547 and then a clamping force is applied to the second electrode 547, so that the opening of the second electrode 547 shrinks inward to clamp the other pin. It can be understood that, in other embodiments not shown, one of the pins may be sandwiched between the first electrode 546 and the bottom base 541, and the other pin is sandwiched between the second electrode 547 and the bottom base 541. In use, the first electrode 546 and the second electrode 547 are respectively connected to the positive and negative electrodes of the battery assembly 60, so that the battery assembly 60 supplies power to the heating member 5451, the heating member 5451 heats the e-liquid absorbed by the liquid guiding member 5452, and then converts the e-liquid into smoke.

In this embodiment, the heating member 5451 is a spiral heating wire, and the liquid guiding member 5452 is made of cotton. It can be understood that, in other embodiments not shown, the heating member 5451 may also be is made of conductive paste, heating tube, heating net, etc; the liquid guiding member 5452 may also made of fiber rope, sponge, porous ceramic, porous graphite, foam metal, etc. The heating member 5451 may also be arranged inside the liquid guiding member 5452, which is not limited here.

It should be noted that because the diameter of the venting section 5441 is smaller than the diameter of the sleeve section 5442, a step (not labelled) is formed between the venting section 5441 and the sleeve section 5442. When the user installs the atomizer 545 into the sleeve section 5442, the atomizer 545 resists against the step, it means that the atomizer 545 has been installed in place, which is convenient for the user to operate.

Figure 20:
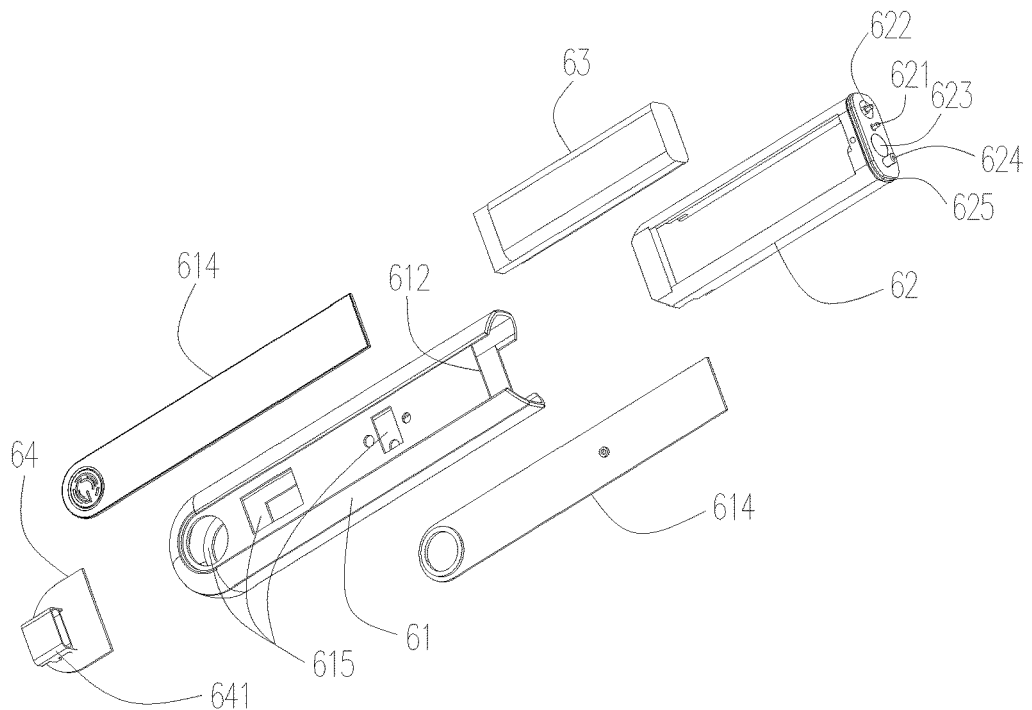
FIG. 20 is an exploded view of the battery assembly of the electronic cigarette shown in FIG. 3.
Figure 21:
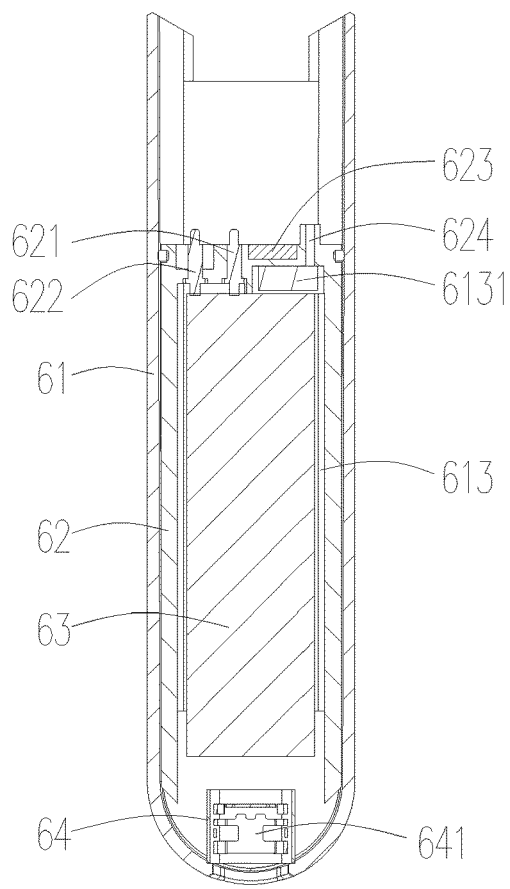
FIG. 21 is a cross-sectional view of the battery assembly of the electronic cigarette of FIG. 3.
Figure 22:
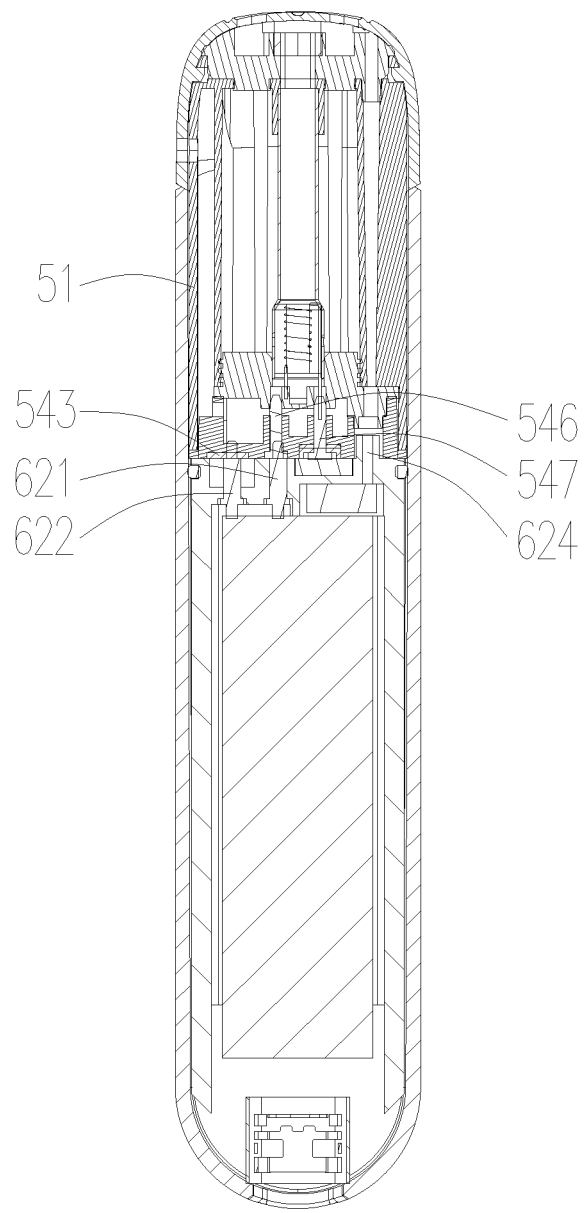
FIG. 22 is a cross-sectional view of the electronic cigarette shown in FIG. 1.

Referring to FIGS. 20, 21 and 22, the battery assembly 60 includes a battery casing 61, a battery holder 62 housed in the battery casing 61, a battery 63 installed on the battery holder 62, and a control board 64 installed on the battery holder 62.

The battery casing 61 substantially has a hollow cylindrical structure with an opening at the upper end, the inner cavity of the battery casing 61 forms a receiving chamber 611, the lower end of the cartridge casing 51 of the cartridge 50 is detachably installed in the upper end of the receiving chamber 611. In this embodiment, the upper end surface of the battery casing 61 is recessed downward along the axial direction of the battery casing 61 to form a guiding groove 612, the lower end surface of the mouthpiece 53 extends downward along the axial direction of the mouthpiece 53 to form a guiding plate 536 matching with the guiding groove 612. When the cartridge 50 is installed into the receiving chamber 611, two opposite sides of the guiding plate 536 can slide along the guiding groove 612, so as to guide the installation of the cartridge 50. When the cartridge 50 is installed in place, the cartridge casing 51 is covered by the battery casing 61, and only the mouthpiece 53 is exposed. In order to facilitate the observation of the amount of e-liquid in the liquid storage chamber 510, the mouthpiece 53 is made of a transparent or translucent material, so that the amount of the e-liquid in the liquid storage chamber 510 can be observed through the mouthpiece 53 and the cartridge casing 51. It can be understood that, in other embodiments not shown, a window may also be defined in the battery casing 61, and the window is aligned with the cartridge casing 51, when the cartridge 50 is installed in place, the cartridge casing 51 can be exposed through the window.

The battery holder 62 is housed in the receiving chamber 611 and located under the cartridge 50. A mounting cavity (not labelled) is provided in the battery holder 62, and the battery 63 is installed in the mounting cavity to fix the battery 63. A first terminal 621 and a second terminal 622 are installed on the upper end of the battery holder 62, the first terminal 621 is electrically connected to one of the positive and negative electrodes of the battery 63, and the second terminal 622 is electrically connected to the other of the positive electrode and negative electrodes of the battery 63. When the cartridge 50 and the battery assembly 60 are installed in place, the first terminal 621 is in contact with and electrically connected to the first electrode 546, and the second terminal 622 is in contact with the conductive sheet 543, so that the second terminal 622 is electrically connected to the second electrode 547 through the conductive sheet 543. Thus, the battery assembly 60 can electrically drive the heating member 5451. In addition, a first magnetic member 623 is installed on the upper end surface of the battery holder 62 corresponding to the second electrode 547. The first magnetic member 623 can attract the second electrode 547, thus, the reliability of the connection between the cartridge 50 and the battery assembly 60 is increased. In this embodiment, the first magnetic member 623 is a magnet. By providing the conductive sheet 543, the arrangement of the first electrode 546, the second electrode 547, the first terminal 621 and the second terminal 622 is more flexible. In this embodiment, when the cartridge 50 is installed in place, the sensor 6131 is located below the second electrode 547, the second terminal 622 cannot pass through the sensor 6131 to be electrically connected to the battery 63. By providing the conductive sheet 543, the second terminal 622 can be arranged on the other side of the battery holder 62 to avoid the sensor 6131. In order to further increase the reliability of the connection between the cartridge 50 and the battery assembly 60, and to rationally use the space on the upper end surface of the battery holder 62, the second terminal 622 is sleeved with a second magnetic member (not labelled), and the second magnetic member is magnetically connected to the conductive sheet 543. It can be understood that, in other embodiments not shown, one of the first magnetic member 623 and the second magnetic member may be omitted, or, both the first magnetic member 623 and the second magnetic part are omitted, and the electronic cigarette can enhance the connection between the cartridge 50 and the battery assembly 60 by other means, for example, the cartridge 50 and the battery assembly 60 are locked together.

The upper end of the battery holder 62 is also protruded to provide with a second connecting column (not labelled), the second connecting column corresponds to the sensing aperture 5414, a sensing groove 624 is defined in the second connecting column along the axial direction of the battery holder 62. A sensing gap 613 is formed between the battery holder 62 and the battery 63, the sensing gap 613 is in communication with the sensing groove 624. When the cartridge 50 and the battery assembly 60 are installed in place, the second connecting column is inserted into the sensing aperture 5414, and the sensing groove 624 is in communication with the sensing hole 5426, such that the sensing gap 613 is in communication with the sensing passage 5161. The arrangement of the second connection column can ensure that the cartridge 50 can only be inserted in a single direction, that is, the cartridge 50 can only be inserted in an upright manner when the sensing aperture 5414 is aligned with the second connection column in order to be smoothly inserted into the battery assembly 60. Otherwise, the cartridge 50 cannot be smoothly inserted into the battery assembly 60 due to the protruding second connecting column. In this way, it can be ensured that when the cartridge 50 is installed in place, the sensing gap 613 is in communication with the sensing passage 5161.

A USB interface 641 is installed on the control board 64, the control board 64 is electrically connected to the battery 63. The lower end surface of the battery casing 61 is provided with an opening corresponding to the USB interface 641, so that the USB interface 641 is exposed through the opening. The user can charge the battery 63 through the USB interface 641. Since the opening is located on the lower end surface of the battery casing 61, it is relatively concealed, making the electronic cigarette more beautiful. The control board 64 is provided with the charging state indication circuit described in the first embodiment. During charging, the charging state of the battery assembly 60 can be accurately indicated. In addition, the USB interface 641 is in communication with the sensing gap 613 and the outside atmosphere. The sensor 6131 is installed in the sensing gap 613, and the sensor 6131 is electrically connected to the control board 64. When the user sucks through the mouthpiece 53, the outside air enters the sensing gap 613 through the USB interface 641, flows further through the sensor 6131, then through the sensing groove 624, the sensing aperture 5414, the sensing hole 5426, the sensing passage 5161, the sensing hole 5241, the sensing slot 528, and the smoke outlet opening 532 in sequence to finally flow out, wherein the sensing aperture 5414, the sensing hole 5426, the sensing passage 5161, the sensing hole 5241 and the sensing slot 528 jointly form a sensing passage. In this embodiment, the sensor 6131 is an airflow sensor, when the airflow sensor detects the airflow, it generates an activation signal and transmits it to the control board 64; the control board 64 controls the battery 63 to supply power to the heating member 5451 after the control board 64 receives the activation signal. It can be understood that, in other embodiments not shown, the sensor 6131 may also be an air pressure sensor, one side of the air pressure sensor is connected to the outside through the USB interface 641 to maintain normal pressure, and the other side produces negative pressure under the action of suction. The air pressure sensor generates a start signal when the pressure difference between the two sides is generated, the air pressure sensor transmits the start signal to the control board 64, the control board 64 can also control the battery 63 to supply power to the heating member 5451 after receiving the start signal. It is understood that in other embodiments not shown, the sensing gap 613 can be also in communication with the outside atmosphere in other ways, for example, a hole is provided in the battery casing. It can be understood that, in other embodiments not shown, in order to prevent false triggering due to the disturbance of the airflow, a threshold can also be set, only when the intensity of the airflow is greater than or equal to the threshold; or, only when the air pressure difference between the two sides is greater than or equal to the threshold, will the sensor 6131 generate the start signal.

In this embodiment, the sensor 6131 is arranged below the upper end surface of the battery holder 62. Specifically, the sensor 6131 is arranged in a sensor installing groove (not labelled) defined in the lower surface of the upper end of the battery holder 62, the sensor installing groove is in communication with the sensing groove 624; in this way, the sensor 6131 is located adjacent to the sensing groove 624 and aligned with the sensing groove 624, it is advantageous for the sensor 6131 to detect the user's suction. For the airflow sensor, since it is far away from the USB interface 641, as long as the user does not inhale through the mouthpiece 53, after the outside atmosphere enters the sensing gap 613 through the USB interface 641 under disturbance, it is difficult to pass through the long sensing gap 613 and further flow through the airflow sensor to trigger the airflow sensor to generate a start signal, thereby preventing false triggering. For the air pressure sensor, the communication path between the air pressure sensor and the mouthpiece 53 is shortened, which is conducive to the sealing of the path, so as to ensure that the gas in the communication path is drawn out by the user, to generate a negative pressure between the air pressure sensor and the side corresponding to the communication path. It can be understood that, the longer the passage, the more difficult it is to ensure the air-tightness of the passage. When the air-tightness of the passage is poor, it will cause interference airflow to enter the passage, making it difficult for the air pressure sensor to generate negative pressure on the side corresponding to the passage.

There are a plurality of notches 615 on the battery casing 61, which saves material while reducing weight. In addition, a decoration plate 614 is installed on the side wall of the battery casing 61 corresponding to the notch 615, and the decoration plate 614 covers the notch 615, which makes the product beautiful and ensures the consistency of the product appearance. In this embodiment, there are two decoration plates 614, and they are respectively installed on two opposite sides of the battery casing 61.

In the electronic cigarette of the present disclosure, when the user inhales through the mouthpiece 53, the outside air enters the atomizing chamber 5444 through the air inlet opening 535, the air inlet hole 517, the air inlet chamber 513, the air inlet groove 5417, the ventilation gap 5420 and the air inlet aperture 5423 in sequence, and is mixed with the generated smoke, and finally flows into the user through the smoke outlet passage 5443, the smoke outlet aperture 5151, the smoke outlet hole 522, the through hole 5252, the opening 534, the air guiding grooves 527, the liquid injection grooves 526 and the smoke outlet openings 532 in sequence, wherein the air inlet opening 535, the air inlet hole 517, the air inlet chamber 513, the air inlet groove 5417, the ventilation gap 5420 and the air inlet aperture 5423 jointly form an air inlet passage (not labelled). It can be seen that the sensing passage is isolated from the air inlet passage and the smoke outlet passage 5443, therefore, smoke will not enter the sensing passage, and thus will not affect the sensor 6131. In addition, since the smoke outlet passage 5443 is provided inside the liquid storage chamber 510, part of the heat of the airflow flowing through the smoke outlet passage 5443 can be transferred to the e-liquid in the liquid storage chamber 510, so that the e-liquid has a certain temperature when it enters the atomizing chamber 5444, the atomization efficiency is improved, the energy consumption is reduced, and the temperature of the airflow flowing out through the smoke outlet opening 532 is also lowered to prevent the user from being scalded. Further, a sealing ring 625 is sandwiched between the battery holder 62 and the battery casing 61. The sealing ring 625 can effectively prevent the airflow from leaking between the battery holder 62 and the battery casing 61 to affect the sensitivity of the sensor 6131. It can be understood that, the sealing ring 625 is a rubber ring or a silicone ring. The upper end surface of the battery holder 62 cooperates with the sealing ring 625 to seal the battery holder 62, the battery 63 and the control board 64, to prevent children from contacting these parts and causing danger, and also to prevent users from arbitrarily modifying the circuit, thereby affecting the use of the electronic cigarette.

Figure 23:
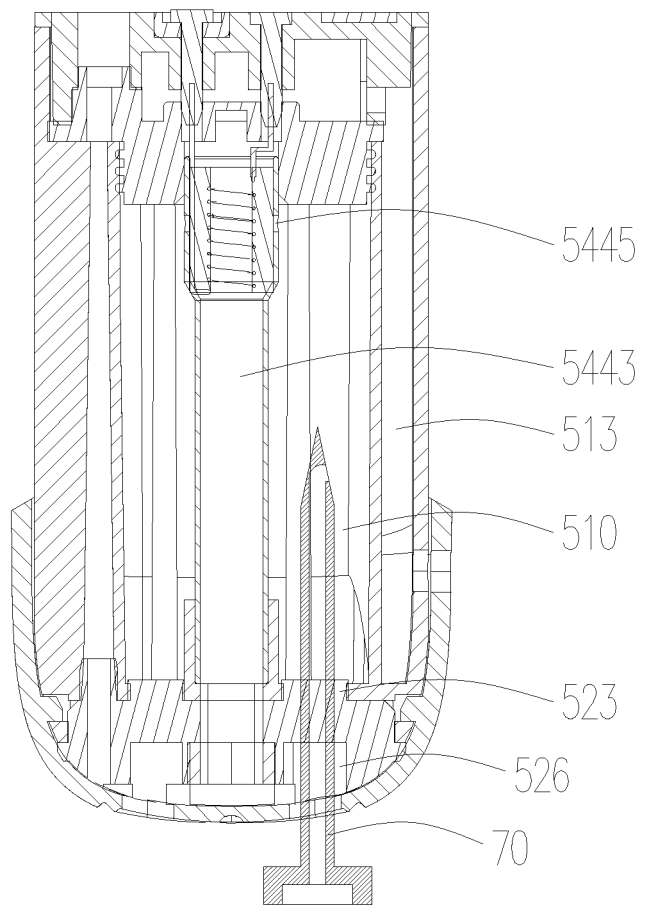
FIG. 23 is a cross-sectional view of the cartridge of the electronic cigarette shown in FIG. 3 in a liquid injection state.

Please refer to FIG. 23, when filling liquid, the cartridge 50 is turned upside down, the liquid injection needle 70 passes through the mouthpiece 53 via the smoke outlet opening 532 and then pierces the sealing element 52, so that one end of the liquid injection needle 70 extends into the liquid storage chamber 510 to inject liquid into the liquid storage chamber 510. In the above process, liquid injection can be carried out without removing the mouthpiece 53 and the sealing element 52, and the operation is simple and the use is convenient. It should be noted that the upside-down of the cartridge 50 refers to the state when the end of the electronic cigarette with the outlet 532 is located below. During the liquid injection process, the air in the liquid storage chamber 510 enters into the atomizing chamber 5444 through the liquid intake hole 5445 and the liquid guiding member 5452, then it is discharged through the air inlet passage or the smoke outlet passage 5443, or it is exhausted simultaneously through the air inlet passage and the smoke outlet passage 5443. The reason why the cartridge 50 is turned upside down during liquid injection is that if the cartridge 50 is placed upright, the e-liquid will first flow to the lower end of the liquid storage chamber 510 near the atomizer 545 under the action of gravity, the e-liquid forms a liquid seal on the liquid intake hole 5445, the gas in the liquid storage chamber 510 cannot be smoothly discharged, and the e-liquid cannot fill up the liquid storage chamber. If the gas in the liquid storage chamber 510 is forced out, the e-liquid may leak under the action of greater pressure. In order to prevent the e-liquid from causing a liquid seal on the liquid intake hole 5445, the cartridge 50 can also be placed horizontally during liquid injection. Alternatively, the liquid storage chamber 510 is filled with a liquid storage member made of porous material, the cartridge 50 can be placed arbitrarily during liquid injection, even if the cartridge 50 is placed upright, it is difficult for the e-liquid to form a liquid seal on the liquid intake hole 5445. This is because it is difficult for the e-liquid to flow downward under the action of gravity due to the absorption of the liquid storage member, and the e-liquid is absorbed in the liquid storage member, so it will not form a liquid seal on the liquid intake hole 5445. In use, the e-liquid in the liquid storage member can be absorbed by the atomizer 545, it is only necessary to ensure that the gas in the liquid storage chamber 510 can be discharged through the liquid intake hole 5445 during the liquid injection process. In addition, the sealing portions 523 and the smoke outlet openings 532 of the sealing element 52 are symmetrically arranged with respect to the central axis of the cartridge 50, which facilitates material management and realizes automatic liquid injection. Specifically, after the cartridge 50 is assembled, the cartridge 50 only needs to be inverted through material handling equipment such as a vibrating screen and a vibrating plate; there is no need to adjust the orientation of the cartridge 50, and the liquid injection needle 70 can always be aligned with one of the sealing portions 523, thereby improving the efficiency of liquid injection. The sealing element 52 is an elastically deformable element, which can be made of a soft material with elastic deformation ability, can be a highly elastic polymer, for example, rubber or silicone, or can be made of a self-healing material. The sealing element 52 can form a seal again after the liquid injection needle 70 is pulled out, thereby sealing the liquid storage chamber 510 to prevent the e-liquid from flowing out. The liquid injection groove 526 reduces the thickness of the portion of the sealing element 52 being pierced through, which is beneficial to the piercing operation of the liquid injection needle 70. It can be understood that, in other embodiments not shown, except for providing the liquid injection hole 5152 at the upper end of the cartridge casing 51, the liquid injection hole 5152 can also be provided in other parts of the cartridge casing 51, for example, the side wall of the cartridge casing 51 or the lower end of the cartridge casing 51, and the sealing element 52 seals the liquid injection hole 5152 correspondingly. That is, the positions of the liquid injection hole 5152 and the sealing element 52 are not limited, it is only necessary to ensure that the liquid can be smoothly injected into the liquid storage chamber 510 and the air in the liquid storage chamber 510 can be smoothly discharged during liquid injection.

In the cartridge 50 provided in the second embodiment of the present disclosure, after the cartridge 50 is assembled, a liquid injection needle 70 is used to pierce the sealing element 52 for performing liquid injection. After the liquid injection is completed, the liquid injection needle 70 is pulled out, and the sealing element 52 restores to seal by itself, which is convenient for users and manufacturers to perform liquid injection operations, and for manufacturers to realize automatic liquid injection. The above process can be realized without disassembling the cigarette 50, and the operation is simple and convenient to use.

In addition, please refer to FIG. 2-1, FIG. 2-2 and FIG. 2-3, from the perspective of the electronic cigarette as a whole, the electronic cigarette is in the form of a long strip, the outer peripheral surface of the electronic cigarette includes a first surface 91 and a second surface 92 opposite to each other, and a third surface 93 and a fourth surface 94 opposite to each other. The first surface 91 and the second surface 92 are symmetrical about the central axis of the electronic cigarette, the third surface 93 and the fourth surface 94 are also symmetrical about the central axis of the electronic cigarette. The first surface 91 and the third surface 93 are connected by a fifth surface 95, the first surface 91 and the fourth surface 94 are connected by a sixth surface 96, the second surface 92 and the third surface 93 are connected by a seventh surface 97, the second surface 92 and the fourth surface 94 are connected by an eighth surface 98. The fifth surface 95, the sixth surface 96, the seventh surface 97, and the eighth surface 98 are all circular arc surfaces. The top end of the outer peripheral surface of the electronic cigarette is covered by the top surface 910 (the upper end surface of the cartridge 50), the bottom end of the outer peripheral surface of the electronic cigarette is covered by the bottom surface 920 (the lower end surface of the battery assembly 60). The first surface 91 and the second surface 92 are wide surfaces, the width of the first surface 91 and the second surface 92 is 10 mm-20 mm, the distance between the first surface 91 and the second surface 92 is 5 mm-15 mm. The design of the wide surface and the narrow distance between the first surface 91 and the second surface 92 makes it easy for the user to hold the electronic cigarette, and the user can directly pinch the first surface 91 and the second surface 92, so that the electronic cigarette can be smoked. It can be understood that, some users like to hold the electronic cigarette, when the user holds the electronic cigarette, his thumb can rest on any one of the fifth surface 95, the sixth surface 96, the seventh surface 97 and the eighth surface 98; since the fifth surface 95, the sixth surface 96, the seventh surface 97 and the eighth surface 98 are all arc surfaces, the transition between the surfaces is relaxed, therefore, the thumb of the user is more comfortable, and the user experience is better. The first surface 91 to the eighth surface 98 of the electronic cigarette gradually shrink inwardly at the end adjacent to the top surface 910 to form the suction end of the mouthpiece 53 (not labelled), to provide smooth transition and small thickness, the user experience is better when the suction end is placed in the user's mouth. The first surface 91 and the second surface 92 are flat surfaces, and the electronic cigarette can be placed on the desktop through one of the first surface 91 and the second surface 92 without rolling randomly.

The electronic cigarette provided in the second embodiment of the present disclosure has all the technical features of the above-mentioned cartridge 50, so it has the same technical effects as the above-mentioned cartridge 50.

Third Embodiment

Figure 24:
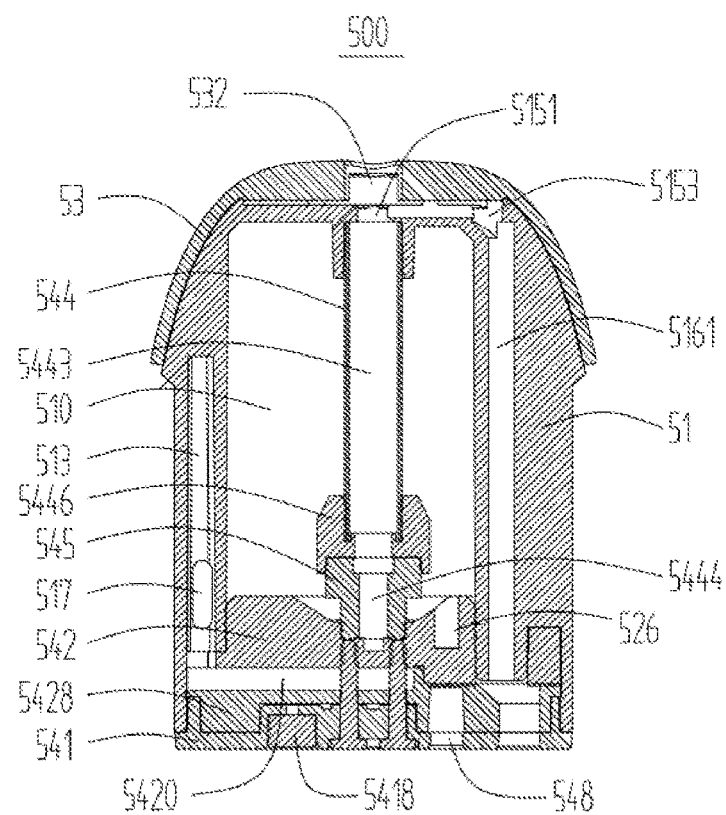
FIG. 24 is a cross-sectional view of the cartridge of the third embodiment of the present disclosure.
Figure 25:
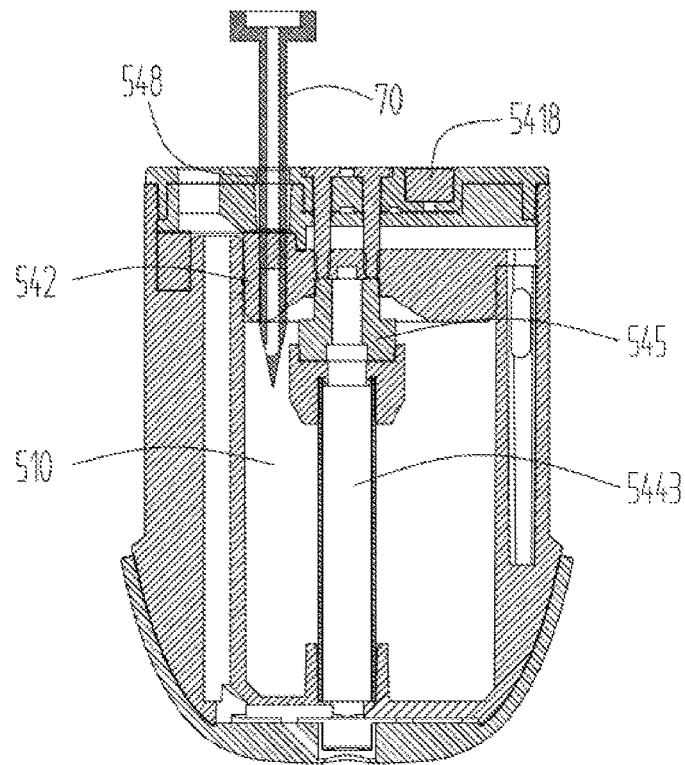
FIG. 25 is a cross-sectional view of the cartridge shown in FIG. 24 in a liquid injection state.

Please refer to FIGS. 24 and 25, the third embodiment of the present disclosure provides an electronic cigarette. The electronic cigarette includes a cartridge 500 and a battery assembly (not shown) electrically connected to the cartridge 500. The cartridge 500 includes a cartridge casing 51 having a liquid storage chamber 510 therein, a mouthpiece 53 installed at one end of the cartridge casing 51, and an atomizing assembly 54 installed at the other end of the cartridge casing 51 opposite to the mouthpiece 53. In use, the atomizing assembly 54 heats the e-liquid stored in the liquid storage chamber 510 under the electric driving of the battery assembly, so that the e-liquid is heated to generate smoke, and the smoke can be inhaled by the user. The difference between the cartridge 500 and the cartridge 50 of the second embodiment is that in this embodiment, the sealing element 52 installed at the top of the cartridge casing 10 is omitted, and at the same time, the structure of the atomizer 545 is different.

In this embodiment, the top of the cartridge casing 51 only has a smoke outlet aperture 5151 and a sensing opening 5153, the smoke outlet aperture 5151 is in communication with the smoke outlet opening 532 and the smoke outlet passage 5443, and the sensing opening 5153 is in communication with the smoke outlet opening 532 and the sensing passage 5161.

The opening at the lower end of the cartridge casing 51 is used as a liquid injection hole, the sealing plug 542 constitutes a sealing element for sealing the liquid storage chamber 510, and liquid is injected through the sealing plug 542, so that the step of opening a hole on the cartridge casing 51 can be saved, and in addition, the sealing element 52 is also omitted. Specifically, the bottom wall of the bottom base 541 is provided with a communication opening 548, the liquid injection needle 70 penetrates the bottom base 541 through the communication opening 548 and then pierces the sealing plug 542, the liquid injection needle 70 is extended into the liquid storage chamber 510, and liquid is injected into the liquid storage chamber 510. Compared with the second embodiment, the structure is simpler. The material of the sealing plug 542 is the same as that of the sealing element 52 of the second embodiment, so that after the liquid injection needle 70 is pulled out, the sealing plug 542 can restore the sealing function by itself. When injecting liquid, it is also needed to turn the cartridge 500 upside down, the e-liquid first fills the end of the liquid storage chamber 510 away from the atomizer 545 under the action of gravity, and does not form a liquid seal. It should be noted that in this embodiment, there is only one communication opening 548 and it is not provided at the central axis position of the cartridge 500, therefore, the communication opening 548 may not align with the liquid injection needle 70 after the cartridge 500 is sorted. A magnetic attraction member 5418 is installed at the bottom of the bottom base 541, the magnetic attraction member 5418 is magnetic or can be magnetically attracted, after the cartridge 500 is turned upside down, the material sorting device can make the direction of the cartridge 500 consistent through magnetic action, so that the communication opening 548 of the cartridge 500 is aligned with the liquid injection needle 70 after sorting. In this embodiment, the magnetic attraction member 5418 is a magnet. It can be understood that, in other embodiments not shown, the magnetic attraction member 5418 can be omitted, and manual sorting can be performed; or, referring to the second embodiment, two communicating openings 548 arranged symmetrically with respect to the central axis of the cartridge 500 are provided. The sealing plug 542 is provided with a liquid injection groove (not labelled), and similarly, the thickness of the portion of the sealing plug 542 that needs to be punctured is reduced to facilitate the puncture of the liquid injection needle 70.

In order to prevent the communication opening 548 from communicating with the ventilation gap 5420, causing gas to leak through the communication opening 548, a vent sealing element 5428 is installed in the communication opening 548, the vent sealing element 5428 separates the ventilation gap 5420 from the communication opening 548. It can be understood that, the material of the vent sealing element 5428 includes but is not limited to silicone or rubber.

In this embodiment, the atomizer 545 is a ceramic heating member, the ceramic heating member has both the function of absorbing liquid and heating. That is, the atomizer 545 is both a liquid guiding member and a heating member. The ceramic heating member includes a porous ceramic member and a heating member sintered in the porous ceramic member. The lower end of the atomizer 545 is connected with the sealing plug 542, the upper end of the atomizer 545 is connected to the vent pipe 544. The atomizer 545 is provided with an atomizing chamber 5444 along the axial direction of the atomizer 545. During the liquid injection process of the cartridge 500, the air in the liquid storage chamber 510 enters into the atomizing chamber 5444 through the atomizer 545, and then is discharged through the air inlet passage or the smoke outlet passage 5443, or it is exhausted simultaneously through the air inlet passage and the smoke outlet passage 5443. After the liquid injection is completed, the atomizer 545 can prevent the leakage of the e-liquid. In addition, a sealing gasket 5446 is installed on the vent pipe 544, the lower end of the vent pipe 544 is sealed and inserted into the upper end of the sealing gasket 5446, the upper end of the atomizer 545 is sealed and inserted into the lower end of the sealing gasket 5446, to prevent the e-liquid from leaking through the connection between the vent pipe 544 and the atomizer 545. The material of the sealing gasket 5446 includes, but is not limited to, silicone or rubber. In addition, the atomizer 545 in this embodiment can also be applied to the second embodiment, and the atomizer 545 in the second embodiment can also be applied to this embodiment. It should be noted that, in this embodiment, since the mouthpiece 53 does not cover the air inlet hole 517, the mouthpiece 53 does not have an air inlet opening 535 correspondingly. Since the air inlet hole 517 is located adjacent to the lower end of the cartridge casing 51, when the cartridge 50 is inserted into the battery assembly 60, the air inlet hole 517 may be shielded by the battery casing 61. In one embodiment, an air inlet opening 535 is defined in the battery casing 61. In another embodiment, a flange is provided on the inner wall of the battery casing 61 and/or on the outer wall of the cartridge casing 51, so that after the cartridge 50 is inserted into the battery assembly 60, a gap is formed between the cartridge casing 51 and the battery casing 61, and the gap communicates with the air inlet hole 517 and the outside atmosphere.

The battery assembly of the third embodiment has the same structure as the battery assembly 60 of the second embodiment, and will not be repeated here. It can be understood that, in other embodiments not shown, the cartridge 500 of the third embodiment can also be equipped with other power supply equipment different from the battery assembly 60.

In the second embodiment, the mouthpiece 53 is used as a shielding member, and the smoke outlet opening 532 is used as a communication opening, so that the user cannot directly touch the sealing element 52, which can prevent children from disassembling the sealing element 52 arbitrarily; but adult users can insert the liquid injection needle 70 into the sealing element 52 through the smoke outlet opening 532 to perform liquid injection. In the third embodiment, the bottom base 541 is used as a shielding member, the bottom base 541 is connected to the cartridge casing 51 and cannot be disassembled to prevent children from contacting the sealing plug 542 and arbitrarily disassembling the sealing plug 542, thereby further contacting the e-liquid. On the other hand, since the shielding member is fixedly connected to the cartridge casing 51, the sealing member (the sealing element 52 in the second embodiment and the sealing plug 542 in the third embodiment) is located between the shielding member and the cartridge casing 51, the shielding member constitutes part of the outer contour of the cartridge 50, 500; therefore, the sealing member is shielded by the shielding member, so that children cannot arbitrarily touch the sealing member. Moreover, the sealing member will not sway randomly under the clamping action of the shielding member and the cartridge casing 51, which prevents the sealing member from moving to cause liquid leakage when the liquid injection needle 70 is pulled out. By using the necessary components of the cartridge 50, 500 such as the mouthpiece 51 or the bottom base 541 as the shielding member, one component has multiple functions, and the arrangement of the structure is more reasonable.

The second embodiment can also refer to the third embodiment, using the sealing plug 542 for liquid injection. In one embodiment, the sensing aperture 5414 is used as a communication opening, the liquid injection needle 70 extends through the sealing plug 542 after passing through the sensing aperture 5414, and then extends into the liquid storage chamber 510 for liquid injection. In another embodiment, the setting position of the air inlet hole 517 is changed, and the air inlet hole 517 is defined in the bottom base 541, at this time, both the air inlet chamber 513 and the air inlet opening 535 can be omitted, the air inlet hole 517 is in communication with the ventilation gap 5420, the air inlet hole 517 is used as a communication opening, and during liquid injection, the liquid injection needle 70 sequentially passes through the air inlet hole 517 and the ventilation gap 54201, and then pierces through the sealing plug 542 and extends into the liquid storage chamber 510 for liquid injection.

The above-mentioned embodiments merely represent several implementations of the present application, and the descriptions thereof are more specific and detailed, but they shall not be understood as a limitation on the scope of the present application. It should be noted that, for those of ordinary skill in the art, variations and improvements may still be made without departing from the concept of the present application, and all of which shall fall into the protection scope of the present application. Therefore, the scope of protection of the present application shall be subject to the appended claims.

What is claimed is:

1. A cartridge, comprising:
    a cartridge casing with a liquid storage chamber therein;
    a sealing element for sealing the liquid storage chamber;
    a mouthpiece provided on the cartridge casing;
    a bottom base;
    a liquid guiding member;
    an atomizing chamber;
    a smoke outlet passage; and
    an air inlet passage;
    wherein the mouthpiece is arranged at one end of the cartridge casing along an axial direction of the cartridge casing, the mouthpiece is provided with a smoke outlet opening, the bottom base is arranged at the other end of the cartridge casing along the axial direction of the cartridge casing opposite to the mouthpiece, the liquid storage chamber is provided in the cartridge casing along the axial direction of the cartridge casing;
    the liquid guiding member is made of porous material, the liquid guiding member is a hollow structure with both ends being opened, an inner cavity of the liquid guiding member forms the atomizing chamber, the liquid guiding member is arranged along the axial direction of the cartridge casing, the liquid guiding member is at least partially received in the liquid storage chamber, the liquid guiding member is located at one end of the liquid storage chamber adjacent to the bottom base, the smoke outlet passage is located in the liquid storage chamber and is isolated from the liquid storage chamber;
    the atomizing chamber is in communication with the liquid storage chamber, the smoke outlet passage and the air inlet passage, the sealing element is located between the mouthpiece and the cartridge casing, the mouthpiece forms part of the outer contour of the cartridge and the sealing element is shielded by the mouthpiece, the smoke outlet opening is defined through the mouthpiece, the sealing element is an elastically deformable member;
    the cartridge casing is provided with two liquid injection holes arranged symmetrically about the center axis of the cartridge, the liquid injection holes are in communication with the liquid storage chamber, a lower end surface of the sealing element is protruded to provide with two sealing portions for respectively sealing the two liquid injection holes, an upper end surface of the sealing element is provided with two liquid injection grooves corresponding to the two sealing portions, there are two smoke outlet openings on the mouthpiece, the two smoke outlet openings are respectively aligned with the two liquid injection grooves;
    when filling liquid, a liquid injection needle passes through the smoke outlet opening and pierces the sealing element, and then extends into the liquid storage chamber to inject e-liquid, and the air in the liquid storage chamber enters into the atomizing chamber and is discharged through the air inlet passage and/or the smoke outlet passage;
    when the liquid injection needle is pulled out after liquid injection, the sealing element automatically restores to seal the liquid storage chamber again.

2. The cartridge according to claim 1, wherein the cartridge further comprises a sealing plug and a vent pipe, the sealing plug seals one end of the liquid storage chamber adjacent to the bottom base, the sealing plug is located between the cartridge casing and the bottom base, the vent pipe is received in the liquid storage chamber, one end of the vent pipe is connected with the liquid guiding member, and the other end of the vent pipe is connected with one end of the cartridge casing provided with the mouthpiece, the smoke outlet passage is formed by the inner cavity of the vent pipe.

3. The cartridge according to claim 2, wherein one end of the vent pipe is sleeved outside the liquid guiding member, the vent pipe is provided with a liquid intake hole in communication with the liquid storage chamber, the liquid guiding member is attached to the inner wall of the vent pipe corresponding to the liquid intake hole, or, one end of the vent pipe resists against the liquid guiding member, the outer peripheral wall of the liquid guiding member is exposed in the liquid storage chamber.

4. The cartridge according to claim 2, wherein an air inlet chamber separated from the liquid storage chamber is provided in the cartridge casing along the axial direction of the cartridge casing, the side wall of the cartridge casing is provided with an air inlet hole, a ventilation gap is formed between the bottom base and the sealing plug, the air inlet chamber is in communication with the air inlet hole and the ventilation gap respectively, the air inlet passage comprises the air inlet hole, the air inlet chamber and the ventilation gap.

5. The cartridge according to claim 2, wherein a sensing passage separated from the liquid storage chamber and the air inlet chamber is provided in the cartridge casing along the axial direction of the cartridge casing, a sensing aperture is defined in the bottom base, the sensing passage is in communication with the sensing aperture and the smoke outlet opening.

6. An electronic cigarette, comprising:
a battery assembly; and
a cartridge according to claim 1, wherein the cartridge is detachably inserted into the battery assembly.

7. A cartridge configured for use in an electronic cigarette comprising a battery assembly, wherein the cartridge comprises an atomizing assembly, the atomizing assembly comprises an atomizer, a conductive sheet, a first electrode and a second electrode, the atomizer comprises a heating member, two ends of the heating member are respectively in contact with the first electrode and the second electrode to achieve electrical connection, the conductive sheet is in contact with the second electrode to achieve electrical connection, the conductive sheet is insulated from the first electrode to achieve electrical isolation, the battery assembly is provided with a first terminal and a second terminal, when the cartridge is connected to the battery assembly, the first terminal is electrically connected to the first electrode, the second terminal is electrically connected to the conductive sheet;
the cartridge further comprises a bottom base, a lower end surface of the bottom base is partially recessed to form a holding groove, the conductive sheet is installed in the holding groove, the first electrode and the second electrode are both inserted into the bottom base from the lower end surface of the bottom base and extend through the bottom base from an upper end surface of the bottom base, the second electrode is located at one side of the first electrode, the conductive sheet is sleeved on the outside of the second electrode, the conductive sheet extends to the other side of the first electrode after bypassing the first electrode.

8. The cartridge according to claim 7, wherein the bottom base has insulation properties, a part of the lower end surface of the bottom base is interposed between the conductive sheet and the first electrode.

9. The cartridge according to claim 7, wherein the upper end of each of the first electrode and the second electrode is provided with an opening, two ends of the heating member respectively extend into the opening of the first electrode and the opening of the second electrode, when a clamping force is applied to the opening of the first electrode and the opening of the second electrode, the opening of the first electrode and the opening of the second electrode clamp both ends of the heating member; or, the two ends of the heating member are respectively sandwiched between the first electrode and the bottom base, and between the second electrode and the bottom base.

10. The cartridge according to claim 7, wherein the atomizing assembly further comprises a sealing plug and a vent pipe, the atomizing member further comprises a liquid guiding member, the sealing plug is arranged on the bottom base, a ventilation gap exists between the sealing plug and the bottom base, one end of the vent pipe is arranged on the sealing plug, the liquid guiding member is accommodated in one end of the vent pipe adjacent to the sealing plug, the inner cavity of the liquid guiding member forms the atomizing chamber, the heating member is received in the atomizing chamber, the inner cavity of the vent pipe forms the smoke outlet passage, the atomizing chamber is in communication with the smoke outlet passage and the ventilation gap.

11. The cartridge of claim 10, wherein the bottom base is provided with a sensing aperture isolated from the ventilation gap.

* * * * *